(12) United States Patent
Motomura et al.

(10) Patent No.: US 9,581,069 B2
(45) Date of Patent: Feb. 28, 2017

(54) MICROPARTICLE DETECTION SYSTEM

(71) Applicant: NGK SPARK PLUG CO., LTD., Nagoya-shi, Aichi (JP)

(72) Inventors: Masayuki Motomura, Komaki (JP); Takeshi Sugiyama, Ichinomiya (JP); Keisuke Tashima, Kasugai (JP); Toshiya Matsuoka, Gifu (JP); Hitoshi Yokoi, Aichi (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 265 days.

(21) Appl. No.: 14/374,247

(22) PCT Filed: Mar. 8, 2013

(86) PCT No.: PCT/JP2013/001509
§ 371 (c)(1),
(2) Date: Jul. 24, 2014

(87) PCT Pub. No.: WO2013/136745
PCT Pub. Date: Sep. 19, 2013

(65) Prior Publication Data
US 2014/0352405 A1  Dec. 4, 2014

(30) Foreign Application Priority Data
Mar. 15, 2012 (JP) ................. 2012-059112

(51) Int. Cl.
*G01N 15/06* (2006.01)
*F01N 11/00* (2006.01)
(Continued)

(52) U.S. Cl.
CPC .......... *F01N 11/00* (2013.01); *G01M 15/102* (2013.01); *G01N 15/0656* (2013.01);
(Continued)

(58) Field of Classification Search
None
See application file for complete search history.

(56) References Cited

U.S. PATENT DOCUMENTS 4,531,486 A * 7/1985 Reif .................. G01N 15/0656
123/198 D
4,607,228 A * 8/1986 Reif ...................... G01N 27/60
324/453

(Continued)

FOREIGN PATENT DOCUMENTS

DK  WO 2005083426 A2 *  9/2005  ............... C12Q 1/04
JP  2001-183334 A  7/2001
(Continued)

OTHER PUBLICATIONS

International Search Report of PCT/JP2013/001509, dated May 14, 2013.

*Primary Examiner* — Andre Allen
(74) *Attorney, Agent, or Firm* — Sughrue Mion, PLLC

(57) ABSTRACT

A particulate detection system (1) for detecting the amount of particulates S in a gas under measurement EG includes a detection section (10), a drive circuit (210, 240), and a drive control section (225). The detection section includes a first potential member (31, 12, 13) maintained at a first potential PV1, a second potential member (14, 51, 53) maintained at a second potential PVE, PV3, and an insulating member (121, 77, 76) disposed between the first and second potential members. The system includes insulation test means (215, S3, 245, S5) for testing the degree of insulation between the first and second potential members. The drive control section includes drive permission/prohibition determination means S4, S6 for determining, on the basis of the degree of insulation tested by the insulation test means, whether to permit the drive of the detection section by the drive circuit.

9 Claims, 12 Drawing Sheets

(51) Int. Cl.
*G01M 15/10* (2006.01)
*G01N 27/68* (2006.01)
*G01N 15/00* (2006.01)
*G01R 31/02* (2006.01)

(52) U.S. Cl.
CPC .......... *G01N 27/68* (2013.01); *F01N 2560/05* (2013.01); *G01N 2015/0046* (2013.01); *G01R 31/025* (2013.01)

(56) References Cited

U.S. PATENT DOCUMENTS

| | | | |
|---|---|---|---|
| 7,406,855 B2 | 8/2008 | Tikkanen et al. | |
| 7,862,649 B2 | 1/2011 | Sakuma et al. | |
| 2004/0227080 A1* | 11/2004 | Hayn | H01J 37/244 250/310 |
| 2006/0156791 A1 | 7/2006 | Tikkanen et al. | |
| 2010/0000404 A1 | 1/2010 | Sakuma et al. | |
| 2011/0050243 A1 | 3/2011 | Tikkanen | |
| 2012/0234172 A1* | 9/2012 | Sugiyama | G01N 15/0656 96/26 |
| 2012/0262182 A1* | 10/2012 | Matsuoka | G01N 15/0656 324/464 |
| 2012/0264064 A1* | 10/2012 | Giomataris | H01J 47/065 430/319 |
| 2013/0219990 A1* | 8/2013 | Allmendinger | G01N 33/0027 73/23.31 |
| 2014/0239185 A1* | 8/2014 | de Oliveira | G01T 1/2935 250/374 |
| 2015/0020574 A1* | 1/2015 | Motomura | G01N 15/0656 73/23.31 |
| 2016/0011093 A1* | 1/2016 | Matsuoka | G01N 15/0656 73/23.33 |

FOREIGN PATENT DOCUMENTS

| | | |
|---|---|---|
| JP | 2005-91043 A | 4/2005 |
| JP | 2007-514923 A | 6/2007 |
| JP | 2011-513742 A | 4/2011 |
| JP | 2012-47722 A | 3/2012 |
| WO | 2008/111677 A1 | 9/2008 |
| WO | 2009/109688 A1 | 9/2009 |

\* cited by examiner

MICROPARTICLE DETECTION SYSTEM

CROSS REFERENCE TO RELATED APPLICATIONS

This application is a National Stage of International Application No. PCT/JP2013/001509 filed Mar. 8, 2013, claiming priority based on Japanese Patent Application No. 2012-059112, filed Mar. 15, 2012, the contents of all of which are incorporated herein by reference in their entirety.

TECHNICAL FIELD

The present invention relates to a particulate (microparticule) detection system for detecting the amount of particulates contained in a gas under measurement which flows through a gas flow pipe.

BACKGROUND ART

Measurement of the amount of particulates contained in a gas is demanded in some situations. For example, exhaust gas discharged from an internal combustion engine (for example, a diesel engine or a gasoline engine) may contain particulates such as soot.

Exhaust gas containing such particulates is purified by means of collecting the particulates through use of a filter. Therefore, if the filter suffers breakage or a like failure, unpurified exhaust gas is discharged directly to the downstream side of the filter.

Therefore, there has been demanded a particulate detection system which can detect the amount of particulates contained in exhaust gas on the downstream side of the filter in order to directly measure the amount of particulates contained in exhaust gas or to detect a failure of the filter.

For example, Patent Document 1 discloses a particulate measurement processing method and apparatus. In the method disclosed in Patent Document 1, an ionized gas containing positive ions is mixed with exhaust gas which is introduced from an exhaust pipe into a channel and which contains particulates, so as to electrify the particulates, and the particulates are then released to the exhaust pipe. A current (signal current) which flows in accordance with the amount of the released, charged particulates is detected so as to detect the particulate concentration.

In such a particulate detection system, a detection section for detecting the amount of particulates generally includes a plurality of conductive members maintained at different potentials, and an insulating member for insulating these conductive members from one another.

PRIOR ART DOCUMENT

Patent Document

Patent Document 1: WO2009/109688

SUMMARY OF THE INVENTION

Problems to be Solved by the Invention

However, a foreign substance contained in a gas under measurement (e.g. soot, water droplets, or the like in the case where the gas under measurement is exhaust gas discharged from an internal combustion engine) may adhere to these members. Also, outside the gas flow pipe, a foreign substance (soot, etc.) contained in the ambient air may adhere to these members, or water droplets may adhere to these members due to splashing of water thereto. In the case where the insulating performance of the insulating member has deteriorated due to adhesion of such a foreign substance to the surface of the insulating member, imprudent driving of a detection section by a drive circuit may result in a failure of the detection section to properly detect the amount of particulates, or a failure of the drive circuit.

The present invention has been accomplished in view of such a problem, and its object is to provide a particulate detection system which detects the amount of particulates when the amount of particulates can be detected properly.

Means for Solving the Problems

One mode of the present invention which solves the above-described problems is a particulate detection system for detecting an amount of particulates in a gas under measurement flowing through a gas flow pipe, comprising a detection section which is mounted to a mounting opening of the gas flow pipe; a drive circuit which drives the detection section; and a drive control section which controls the drive circuit, wherein the detection section includes a first potential member which is maintained at a first potential when the detection section is driven by the drive circuit, a second potential member which is maintained at a second potential different from the first potential when the detection section is driven by the drive circuit, and an insulating member which is disposed between the first potential member and the second potential member so as to electrically insulate them from each other. The system further comprises insulation test means for testing the degree of insulation between the first potential member and the second potential member. The drive control section includes drive permission/prohibition determination means for determining, on the basis of the degree of insulation tested by the insulation test means, whether to permit the drive of the detection section by the drive circuit.

In the particulate detection system of claim 1, the detection section includes a first potential member maintained at a first potential, a second potential member maintained at a second potential, and an insulating member for insulating them from each other.

The insulation test means tests the degree of insulation between the first potential member and the second potential member, and the drive permission/prohibition determination means determines, on the basis of the tested degree of insulation, whether to permit the drive of the detection section by the drive circuit.

Examples of the first potential member, the second potential member, and the insulating member include not only those exposed to the gas under measurement but also those exposed to the air outside the gas flow pipe.

An example of the insulation test means for testing the degree of insulation is means for applying a test voltage between the first potential member and the second potential member and measuring a leak current flowing between the two members (through the insulating member) or an insulation resistance between the two members. Another example of the insulation test means is means for measuring a capacitance between the first potential member and the second potential member by using a capacitance meter or the like.

Preferably, the degree of insulation (whether the insulating performance is high or not (low)) is determined through comparison with an insulating performance reference value which changes in accordance with the ambient temperature, humidity, or the temperature of the gas under measurement, or with a fixed insulating performance reference value determined in advance.

Notably, a reference value for leak current, a reference value for insulation resistance, or a reference value for capacitance may be used as the insulating performance reference value, depending on, for example, the method of testing the degree of insulation (insulating performance).

According to a particulate detection system of claim 2, the above-described particulate detection system is preferably configured such that the drive control section includes drive stoppage means for stopping the drive of the detection section by the drive circuit when the degree of insulation tested by the insulation test means is low.

According to a particulate detection system of claim 3, the above-described particulate detection system is preferably configured such that the insulation test means is first test means for applying a test voltage between the first potential member and the second potential member and measuring a leak current flowing between the two members or an insulation resistance between the two members.

According to a particulate detection system of claim 4, any of the above-described particulate detection systems is preferably configured as follows. The detection section includes an ion source which has a first discharge electrode and a second discharge electrode and which produces ions by gaseous discharge between these electrodes, a particulate electrifying section which electrically communicates with the first discharge electrode of the ion source and which is configured to mix a portion of the gas under measurement flowing through the gas flow pipe with the ions produced by the ion source and to return to the gas flow pipe electrified particulates which are particulates contained in the part of the gas under measurement and to which the ions adhere, the particulate electrifying section forming a capturing electrode which captures floating ions which are a portion of the ions and which did not adhere to the particulates, a first communicating member which electrically communicates with the first discharge electrode and the particulate electrifying section, a second discharge electrode communicating member which electrically communicates with the second discharge electrode, and a ground potential member which is the second potential member and which is in contact with and electrically communicates with the gas flow pipe and is maintained at a ground potential which is the second potential. The first discharge electrode of the ion source, the particulate electrifying section, and the first communicating member serve as the first potential member which is maintained at the first potential. The insulating member intervenes between the first potential member and the gas flow pipe or the ground potential member. The drive circuit has a first output terminal for supplying electricity to the first discharge electrode of the ion source and the particulate electrifying section through the first communicating member when the detection section is driven, whereby the first discharge electrode and the particulate electrifying section are maintained at the first potential, and a second output terminal for supplying electricity to the second discharge electrode of the ion source through the second discharge electrode communicating member when the detection section is driven such that the second discharge electrode is maintained at a second discharge potential at which discharge occurs between the first discharge electrode and the second discharge electrode. The drive circuit includes an ion source drive circuit which drives the ion source and the particulate electrifying section. The drive permission/prohibition determination means determines whether to permit the drive of the ion source and the particulate electrifying section by the ion source drive circuit, on the basis of the degree of insulation between the first potential member, and the gas flow pipe and the ground potential member tested by the insulation test means.

This system has a particulate electrifying section, and can detect the amount of particulates from the amount of charge adhering to electrified particulates returned to the gas flow pipe. Namely, the magnitude of a signal current flowing between the first potential which is the potential of the particulate electrifying section and the ground potential of the gas flow pipe corresponds to the amount of charge released from the particulate electrifying section. Therefore, if the degree of insulation between the first communicating member maintained at the first potential and the gas flow pipe or the ground potential member maintained at the ground potential is low, detection of the signal current becomes difficult, and proper detection of the amount of particulates becomes impossible.

Notably, an example of gaseous discharge generated in the ion source is corona discharge. Also, two electrodes for discharge may be disposed such that the two electrodes face each other and gaseous discharge occurs therebetween, or may be disposed such that the two electrodes are located adjacent to each other on a substrate and (gaseous) creeping discharge occurs therebetween.

According to a particulate detection system of claim 5, the above-described particulate detection system preferably comprises a first switch which is disposed between the first output terminal and the first communicating member and which establishes and breaks electrical continuity between the first output terminal and the first communicating member; a second switch which is disposed between the second output terminal and the second discharge electrode communicating member and which establishes and breaks electrical continuity between the second output terminal and the second discharge electrode communicating member; drive-time switch closing instruction means for closing the first switch and the second switch when the detection section is driven; and test-time switch opening instruction means for opening the first switch and the second switch when the degree of insulation between the first potential member, and the gas flow pipe and the ground potential member is tested by the insulation test means.

According to a particulate detection system of claim 6, any of the above-described particulate detection systems is preferably configured as follows. The detection section includes an ion source which has a first discharge electrode and a second discharge electrode and which produces ions by gaseous discharge between these electrodes, a particulate electrifying section which electrically communicates with the first discharge electrode of the ion source and which is configured to mix a portion of the gas under measurement flowing through the gas flow pipe with the ions produced by the ion source and to return to the gas flow pipe electrified particulates which are particulates contained in the part of the gas under measurement and carrying the ions adhering to the particulates, the particulate electrifying section forming a capturing electrode which captures floating ions which are a portion of the ions and which did not adhere to the particulates, a first communicating member which electrically communicates with the first discharge electrode and the particulate electrifying section, an auxiliary electrode which is electrically insulated from the first discharge electrode and the second discharge electrode and which is disposed within the particulate electrifying section so as to assist the capturing of the floating ions by the capturing electrode, and an auxiliary electrode communicating member which electrically communicates with the auxiliary electrode. The first discharge electrode of the ion source, the particulate electrifying section, and the first communicating member serve as the first potential member which is maintained at the first potential. The auxiliary electrode and the auxiliary electrode communicating member serve as an auxiliary potential member which is the second potential member and is maintained at an auxiliary electrode potential which is the second potential. The insulating member is disposed between the particulate electrifying section and the auxiliary electrode communicating member. The drive circuit has an auxiliary first output terminal which electrically communicates with the first discharge electrode of the ion source and the particulate electrifying section through the first communicating member when the detection section is driven, whereby the auxiliary first output terminal is maintained at the first potential, and an auxiliary second output terminal for supplying electricity to the auxiliary electrode via the auxiliary electrode communicating member when the detection section is driven such that the auxiliary electrode is maintained at the auxiliary electrode potential. The drive circuit includes an auxiliary electrode drive circuit which drives the auxiliary electrode. The drive permission/prohibition determination means determines whether to permit the drive of the auxiliary electrode by the auxiliary electrode drive circuit, on the basis of the degree of insulation between the first potential member, and the auxiliary potential member tested by the insulation test means.

This system includes the above-mentioned ion source and particulate electrifying section. Accordingly, the amount of particulates can be detected from the amount of charge adhering to electrified particulates returned to the gas flow pipe.

Namely, the magnitude of the signal current flowing between the first potential which is the potential of the particulate electrifying section and the potential of the gas flow pipe corresponds to the amount of charge released from the particulate electrifying section. In addition, this system includes an auxiliary electrode. This auxiliary electrode assists capturing of floating ions by the capturing electrode of the particulate electrifying section. Accordingly, if the degree of insulation between the particulate electrifying section and the auxiliary potential member decreases and the auxiliary electrode potential decreases accordingly, floating ions cannot be captured properly, and not only the electrified particulates but also the floating ions are released from the particulate electrifying section to the gas flow pipe, which may decrease the detection accuracy of the amount of particulates.

According to a particulate detection system of claim 7, the above-described particulate detection systems preferably comprises an auxiliary first switch which is disposed between the auxiliary first output terminal and the first communicating member and which establishes and breaks electrical continuity between the auxiliary first output terminal and the first communicating member; an auxiliary second switch which is disposed between the auxiliary second output terminal and the auxiliary electrode communicating member and which establishes and breaks electrical continuity between the auxiliary second output terminal and the auxiliary electrode communicating member; drive-time auxiliary switch closing instruction means for closing the auxiliary first switch and the auxiliary second switch when the detection section is driven; and test-time auxiliary switch opening instruction means for opening the auxiliary first switch and the auxiliary second switch when the degree of insulation between the first potential member, and the auxiliary potential member is tested by the insulation test means.

According to a particulate detection system of claim 8, the above-described particulate detection system preferably comprises a heater for heating the insulating member; a heater energization circuit for supplying electricity to the heater; and a heater energization control section for controlling the heater energization circuit, wherein the heater energization control section includes insulation recovery energization instruction means, operable when the degree of insulation tested by the insulation test means is low, for instructing the heater energization circuit to supply electricity to the heater so as to heat the insulating member, to thereby recover the degree of insulation.

According to a particulate detection system of claim 9, the above-described particulate detection system is preferably configured such that the gas flow pipe is an exhaust pipe of an internal combustion engine; and the gas under measurement is exhaust gas flowing through the exhaust pipe.

Effects of the Invention

The particulate detection system of claim 1 can detect the amount of particulates by driving the detection section in a state in which the degree of insulation between the first potential member and the second potential member is high. Therefore, the amount of particulates can be detected properly. Also, the system can prevent failure of the drive circuit or the like, which failure would otherwise occur as a result of the drive circuit being driven in a state in which the degree of insulation is low.

In the particulate detection system of claim 2, when the tested degree of insulation is low, the drive of the detection section by the drive circuit is stopped. By virtue of this, when the degree of insulation is low, in particular, when the degree of insulation is extremely low (a short circuit is formed), it is possible to reliably prevent occurrence of problems such as failure of the drive circuit itself and failure of the detection section, which failures would otherwise occur due to drive of the drive circuit.

In the particulate detection system of claim 3, a test voltage is applied between the first potential member and the second potential member, and the degree of insulation between the first potential member and the second potential member is tested on the basis of the leak current flowing between the two members or the insulation resistance between the two members.

Since this method requires application of the test voltage between the first potential member and the second potential member and detection of the current or the resistance, the degree of insulation can be readily tested.

In the particulate detection system of claim 4, the insulation test means tests the degree of insulation between the first communicating member which electrically communicates with the first discharge electrode of the ion source and the particulate electrifying section and which serves as the first potential member, and the gas flow pipe and the ground potential member which communicates with the gas flow pipe, which serves as the second potential member, and which is maintained at the ground potential. The drive permission/prohibition determination means determines, on the basis of the degree of insulation, whether to permit the drive of the ion source and the particulate electrifying section by the ion source drive circuit. By virtue of this, the amount of particulates can be detected properly, and failure of the ion source drive circuit can be prevented.

In the particulate detection system of claim 5, a first switch is provided between the first output terminal and the first communicating member, and a second switch is provided between the second output terminal and the second discharge electrode communicating member. When the detection section is driven, since these switches are closed, the detection section (the ion source, the particulate electrifying section) can be driven by the ion source drive circuit. Meanwhile, in the case where the degree of insulation between the first potential member and "the gas flow pipe and the ground potential member" is tested, the first and second switches are opened. As a result, the ion source drive circuit is disconnected. Therefore, the ion source drive circuit can be protected from the test voltage which is applied when the degree of insulation is tested. In addition, the degree of insulation between the first potential member, and the gas flow pipe and the ground potential member can be tested properly without being affected by the ion source drive circuit.

In the particulate detection system of claim 6, the insulation test means tests the degree of insulation between "the first discharge electrode of the ion source and the particulate electrifying section (the first potential member)" and "the auxiliary electrode and the auxiliary electrode communicating member (the second potential member, the auxiliary potential member)." The drive permission/prohibition determination means determines, on the basis of the degree of insulation, whether to permit the drive of the auxiliary electrode by the auxiliary electrode drive circuit. By virtue of this, the amount of particulates can be detected properly, and failure of the auxiliary electrode drive circuit can be prevented.

In the particulate detection system of claim 7, an auxiliary first switch is provided between the auxiliary first output terminal and the first communicating member, and an auxiliary second switch is provided between the auxiliary second output terminal and the auxiliary electrode communicating member. When the detection section is driven, since these switches are closed, the auxiliary electrode can be driven. Meanwhile, in the case where the degree of insulation between the first potential member and the auxiliary potential member is tested, these switches are opened. As a result, the auxiliary electrode drive circuit is disconnected. Therefore, the auxiliary electrode drive circuit can be protected from the test voltage which is applied when the degree of insulation is tested. In addition, the degree of insulation between the first potential member and the auxiliary potential member can be tested properly without being affected by the auxiliary electrode drive circuit.

In the particulate detection system of claim 8, in the case where the degree of insulation between the first potential member and the second potential member is low, the heater is energized so as to heat the insulating member to thereby recover the insulating performance of the insulating member. Namely, through heating, foreign substances such as water droplets and soot adhering to the insulating member are removed, whereby its insulating performance is recovered. By virtue of this, the present system can perform stable measurement for the gas under measurement which contains foreign substances such as water and soot.

The exhaust gas (the gas under measurement) flowing through an exhaust pipe of an internal combustion engine may contain a large amount of soot (particulates) and water droplets (in particular, at the time of startup). Therefore, as a result of accumulation of soot on, or adhesion of water droplets to, the insulating member which insulates the first potential member and the second potential member from each other, the insulation performance of the insulating member; i.e., the degree of insulation between the first potential member and the second potential member, is likely to decrease, which raises the possibility that, even when the detection section is driven, the amount of particulates cannot be detected properly.

In contrast, in the particulate detection system of claim 9, the degree of insulation between the first potential member and the second potential member is tested, and the determination as to whether to permit the drive of the detection section is made on the basis of the degree of insulation. Therefore, the amount of particulates contained in exhaust gas can be detected properly.

MODE FOR CARRYING OUT THE INVENTION

Figure 1:
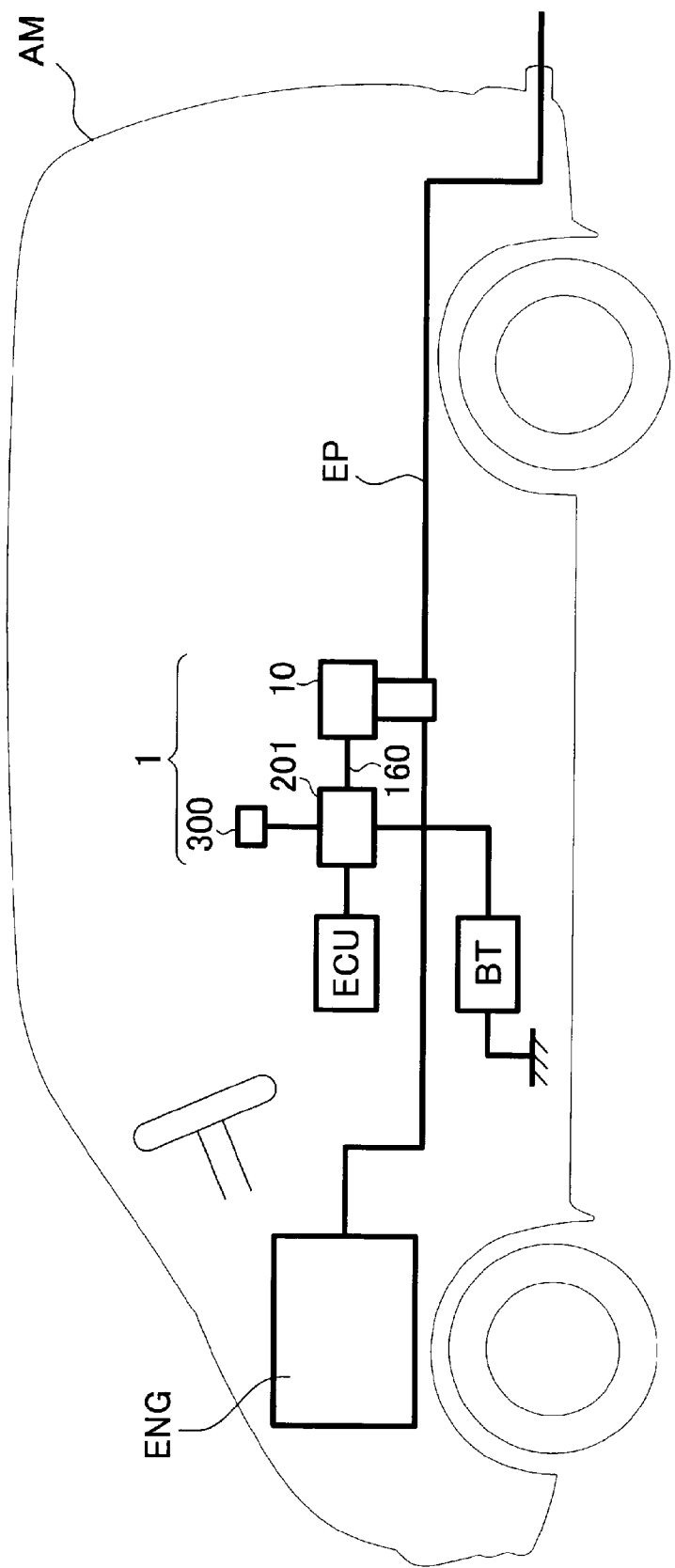
FIG. 1 Explanatory view showing a particulate detection system according to an embodiment which is applied to an exhaust pipe of an engine mounted on a vehicle.

A particulate detection system 1 according to the present embodiment will be described with reference to the drawings. The particulate detection system 1 of the present embodiment is attached to an exhaust pipe EP of an engine ENG (an internal combustion engine) mounted on a vehicle AM, and detects the amount of particulates S (soot, etc.) contained in the exhaust gas EG flowing through the exhaust pipe EP (see FIG. 1). This system 1 is mainly composed of a detection section 10, a circuit section 201, and a feed pump 300 which is a compressed air source for producing compressed air AK (see FIG. 2).

The detection section 10 is attached to a mount portion EPT of the exhaust pipe EP (a gas flow pipe) where a mount opening EPO is formed. A portion of the detection section 10 (located on the right side (the distal end side) of the mount portion EPT in FIG. 2) extends into the interior of the exhaust pipe EP through the mount opening EPO and is to come into contact with the exhaust gas EG (a gas under measurement).

Outside the exhaust pipe EP, the circuit section 201 is connected to the detection section 10 through a cable 160 composed of a plurality of wires. This circuit section 201 includes a circuit which drives the detection section 10 and detects a signal current Is which will be described later.

First, the electrical configuration of the circuit section 201 of the present system 1 will be described with reference to FIGS. 2 and 3. The circuit section 201 includes a measurement control circuit 220 including a signal current detection circuit 230 and a heater energization circuit 226, an ion source power supply circuit 210 (an ion source drive circuit), an auxiliary electrode power supply circuit 240 (an auxiliary electrode drive circuit), a ground insulation test circuit 215, an auxiliary electrode insulation test circuit 245, a first relay RL1, and a second relay RL2.

The ion source power supply circuit 210 (the ion source drive circuit) has a first output terminal 211 maintained at a first discharge potential PV1 and a second output terminal 212 maintained at a second discharge potential PV2. Specifically, the second discharge potential PV2 is maintained at a positive high potential in relation to the first discharge potential PV1. More specifically, a pulse voltage (1 to 2 kV0-p) which is positive in relation to the first discharge potential PV1 is output from the second output terminal 212. The pulse voltage is obtained through half-wave rectification of a sinusoidal wave of about 100 kHz.

Notably, the ion source power supply circuit 210 constitutes a constant-current power supply whose output current is feedback-controlled such that the output current (rms value) is autonomously maintained at a predetermined current value (for example, 5 μA).

The auxiliary electrode power supply circuit 240 (the auxiliary electrode drive circuit) has an auxiliary first output terminal 241 which is maintained at the first discharge potential PV1, and an auxiliary second output terminal 242 which is maintained at an auxiliary electrode potential PV3. Specifically, the auxiliary electrode potential PV3 is set to a potential of, for example, DC 100 to 200 V which is a positive high DC potential in relation to the first discharge potential PV1 but is lower than the peak potential (1 to 2 kV) of the second discharge potential PV2.

A signal current detection circuit 230, which partially constitutes the measurement control circuit 220, has a signal input terminal 231 connected to the first output terminal 211 of the ion source power supply circuit 210, and a ground input terminal 232 connected to a ground potential PVE. This signal current detection circuit 230 is a circuit for detecting the signal current Is which will be described later.

The first relay RL1 has two-pole transfer contacts which form a first switch 213 and a second switch 214. The ground insulation test circuit 215 has a first test terminal 216 and a second test terminal 217.

When the coil (not shown) of the first relay RL1 is not energized, the electrical continuity between the terminals c and b of the first switch 213 is established (the circuit between the terminals c and b is closed), whereby the first output terminal 211 of the ion source power supply circuit 210 and the signal input terminal 231 of the signal current detection circuit 230 are connected to a first potential wiring line 165 of the cable 160 via an inner circuit casing 250. Meanwhile, the electrical continuity between the terminals c and a of the first switch 213 is broken, whereby the first test terminal 216 of the ground insulation test circuit 215 is disconnected from the inner circuit casing 250 and the first potential wiring line 165 of the cable 160. Also, the electrical continuity between the terminals c and b of the second switch 214 is established (the circuit between the terminals c and b is closed), whereby the second output terminal 212 of the ion source power supply circuit 210 is connected to a second potential wiring line 161 of the cable 160.

In contrast, when the coil of the first relay RL1 is energized, the electrical continuity between the terminals c and b of the first switch 213 is broken (the circuit between the terminals c and b is opened), whereby the first output terminal 211 of the ion source power supply circuit 210 and the signal input terminal 231 of the signal current detection circuit 230 are disconnected from the inner circuit casing 250 and the first potential wiring line 165 of the cable 160. Meanwhile, the electrical continuity between the terminals c and a of the first switch 213 is established, whereby the first test terminal 216 of the ground insulation test circuit 215 is connected to the first potential wiring line 165 of the cable 160 via the inner circuit casing 250. Also, the electrical continuity between the terminals c and b of the second switch 214 is broken (the circuit between the terminals c and b is opened) (the electrically continuity between the terminals c and a is established), whereby the second output terminal 212 of the ion source power supply circuit 210 is disconnected from the second potential wiring line 161 of the cable 160.

Notably, the second test terminal 217 of the ground insulation test circuit 215 is connected to the ground input terminal 232 of the signal current detection circuit 230, whereby the second test terminal 217 is maintained at the ground potential PVE.

The second relay RL2 has two-pole transfer contacts which form an auxiliary first switch 243 and an auxiliary second switch 244. Also, the auxiliary electrode insulation test circuit 245 has an auxiliary first test terminal 246 and an auxiliary second test terminal 247. When the coil (not shown) of the second relay RL2 is not energized, the electrical continuity between the terminals c and b of the auxiliary first switch 243 is established (the circuit between the terminals c and b is closed), whereby the auxiliary first output terminal 241 of the auxiliary electrode power supply circuit 240 is connected to the first potential wiring line 165 of the cable 160 via the inner circuit casing 250. Meanwhile, the electrical continuity between the terminals c and a of the auxiliary first switch 243 is broken, whereby the auxiliary first test terminal 246 of the auxiliary electrode insulation test circuit 245 is disconnected from the inner circuit casing 250 and the first potential wiring line 165 of the cable 160. Also, the electrical continuity between the terminals c and b of the auxiliary second switch 244 is established (the circuit between the terminals c and b is closed), whereby the auxiliary second output terminal 242 of the auxiliary electrode power supply circuit 240 is connected to an auxiliary potential wiring line 162 of the cable 160. Meanwhile, the electrical continuity between the terminals c and a of the auxiliary second switch 244 is broken, whereby the auxiliary second test terminal 247 of the auxiliary electrode insulation test circuit 245 is disconnected from the auxiliary potential wiring line 162 of the cable 160.

In contrast, when the coil of the second relay RL2 is energized, the electrical continuity between the terminals c and b of the auxiliary first switch 243 is broken (the circuit between the terminals c and b is opened), whereby the auxiliary first output terminal 241 of the auxiliary electrode power supply circuit 240 is disconnected from the inner circuit casing 250 and the first potential wiring line 165 of the cable 160. Meanwhile, the electrical continuity between the terminals c and a of the auxiliary first switch 243 is established, whereby the auxiliary first test terminal 246 of the auxiliary electrode insulation test circuit 245 is connected to the first potential wiring line 165 of the cable 160 via the inner circuit casing 250. Also, the electrical continuity between the terminals c and b of the auxiliary second switch 244 is broken (the circuit between the terminals c and b is opened), whereby the auxiliary second output terminal 242 of the auxiliary electrode power supply circuit 240 is disconnected from the auxiliary potential wiring line 162 of the cable 160. Meanwhile, the electrical continuity between the terminals c and a of the auxiliary second switch 244 is established, whereby the auxiliary second test terminal 247 of the auxiliary electrode insulation test circuit 245 is connected to the auxiliary potential wiring line 162 of the cable 160.

The heater energization circuit 226 is a circuit for energizing a heater 78 (which will be described later) by PWM control. The heater energization circuit 226 has a first heater energization terminal 226a connected to a first heater connection wiring line 169a of the cable 160, and a second heater energization terminal 226b connected to a second heater connection wiring line 169b of the cable 160.

In the drive processing circuit 201, the ion source power supply circuit 210, the auxiliary electrode power supply circuit 240, the ground insulation test circuit 215, the auxiliary electrode insulation test circuit 245, the first relay RL1, and the second relay RL2 are surrounded by the inner circuit casing 250, which is maintained at the first discharge potential PV1. The terminal c of the first switch 213 (the first relay RL1) and the terminal c of the auxiliary first switch 243 (the second relay RL2) are connected to the inner circuit casing 250.

Notably, in the present embodiment, the inner circuit casing 250 accommodates and surrounds the ion source power supply circuit 210, the auxiliary electrode power supply circuit 240, the ground insulation test circuit 215, the auxiliary electrode insulation test circuit 245, the first relay RL1, the second relay RL2, and a secondary-side core 271B of an isolation transformer 270, and electrically communicates with the first potential wiring line 165 of the cable 160.

The isolation transformer 270 has a core 271 which is divided into a primary-side core 271A, around which a primary-side coil 272 is wound, and the above-mentioned secondary-side core 271B, around which a power-supply-circuit-side coil 273 and an auxiliary-electrode-power-supply-side coil 274 are wound. The primary-side core 271A electrically communicates with the ground potential PVE, and the secondary-side core 271B electrically communicates with the first discharge potential PV1 (the first output terminal 211 of the ion source power supply circuit 210).

The measurement control circuit 220 including the signal current detection circuit 230 and the heater energization circuit 226, the ion source power supply circuit 210, the auxiliary electrode power supply circuit 240, the ground insulation test circuit 215, the auxiliary electrode insulation test circuit 245, the first relay RL1, the second relay RL2, and the inner circuit casing 250 are surrounded by an outer circuit casing 260, which electrically communicates with the ground input terminal 232 of the signal current detection circuit 230 and is maintained at the ground potential PVE. The ground input terminal 232 of the signal current detection circuit 230 and the primary-side core 271A of the isolation transformer 270 are connected to the outer circuit casing 260.

Notably, in the present embodiment, the outer circuit casing 260 accommodates and surrounds the ion source power supply circuit 210, the auxiliary electrode power supply circuit 240, the ground insulation test circuit 215, the auxiliary electrode insulation test circuit 245, the first relay RL1, the second relay RL2, the inner circuit casing 250, the measurement control circuit 220, and the primary-side core 271A of the isolation transformer 270, and electrically communicates with a ground potential wiring line 167 of the cable 160.

The measurement control circuit 220 includes a regulator power supply PS. This regulator power supply PS is driven by an external battery BT through a power supply wiring line BC.

The measurement control circuit 220 includes a microprocessor 202, and can communicate, through a communication line CC, with a control unit ECU which controls the internal combustion engine. Thus, the measurement control circuit 220 can transmit to the control unit ECU a signal which represents the result of measurement by the above-mentioned signal current detection circuit 230 (the magnitude of the signal current Is), a value which is converted therefrom and represents the amount of particulates, etc., or the result of determination as to whether or not the amount of particulates exceeds a predetermined amount. This enables the control unit ECU to control the internal combustion engine and perform other operations such as issuance of a warning which reports a failure of a filter (not shown).

A portion of the electric power externally supplied to the measurement control circuit 220 via the regulator power supply PS is distributed to the ion source power supply circuit 210 and the auxiliary electrode power supply circuit 240 via the isolation transformer 270. Notably, in the isolation transformer 270, the primary-side coil 272, which is a portion of the measurement control circuit 220, the power-supply-circuit-side coil 273, which is a portion of the ion source power supply circuit 210, the auxiliary-electrode-power-supply-side coil 274, which is a portion of the auxiliary electrode power supply circuit 240, and the core 271 (the primary-side core 271A and the secondary-side core 271B) are isolated from one another. Therefore, whereas electric power can be distributed from the measurement control circuit 220 to the ion source power supply circuit 210 and the auxiliary electrode power supply circuit 240, the insulation thereamong can be maintained.

Notably, in the present embodiment, the isolation transformer 270 also serves as an auxiliary electrode isolation transformer for supplying electric power to the auxiliary electrode power supply circuit 240.

Meanwhile, as in the case of the measurement control circuit 220, the ground insulation test circuit 215 and the auxiliary electrode insulation test circuit 245 receive the electric power supplied from the regulator power supply PS through an unillustrated power wiring line.

The feed pump 300 takes in atmosphere (air) therearound, and feeds clean, compressed air AK toward an ion gas jetting source 11, which will be described later, through an air feed pipe 310 whose distal end portion is inserted into the outer circuit casing 260 and the inner circuit casing 250.

Next, the cable 160 will be described (see FIG. 2). The second potential wiring line 161, the auxiliary potential wiring line 162, the first heater connection wiring line 169a, and the second heater connection wiring line 169b, which are formed of copper wire, and a hollow air pipe 163 formed of resin are disposed at the center of the cable 160. These wiring lines and pipe are circumferentially surrounded by an inner insulator layer 164.

Further, this inner insulator layer 164 is circumferentially surrounded by the first potential wiring line 165 formed of braided thin copper wires. In addition, an insulator cover layer 166 which is formed of an insulating resin is disposed around the first potential wiring line 165. The circumference of the insulator covering layer 166 is covered with the ground potential wiring line 167 formed of braided thin copper wires. Notably, an outer insulating cover layer 168 formed of an insulating resin is formed around the ground potential wiring line 167 so as to protect the ground potential wiring line 167.

In addition, this cable 160 allows a gas to flow through a gas flow passage 163H of the air pipe 163 in the longitudinal direction of the cable 160.

Figure 2:
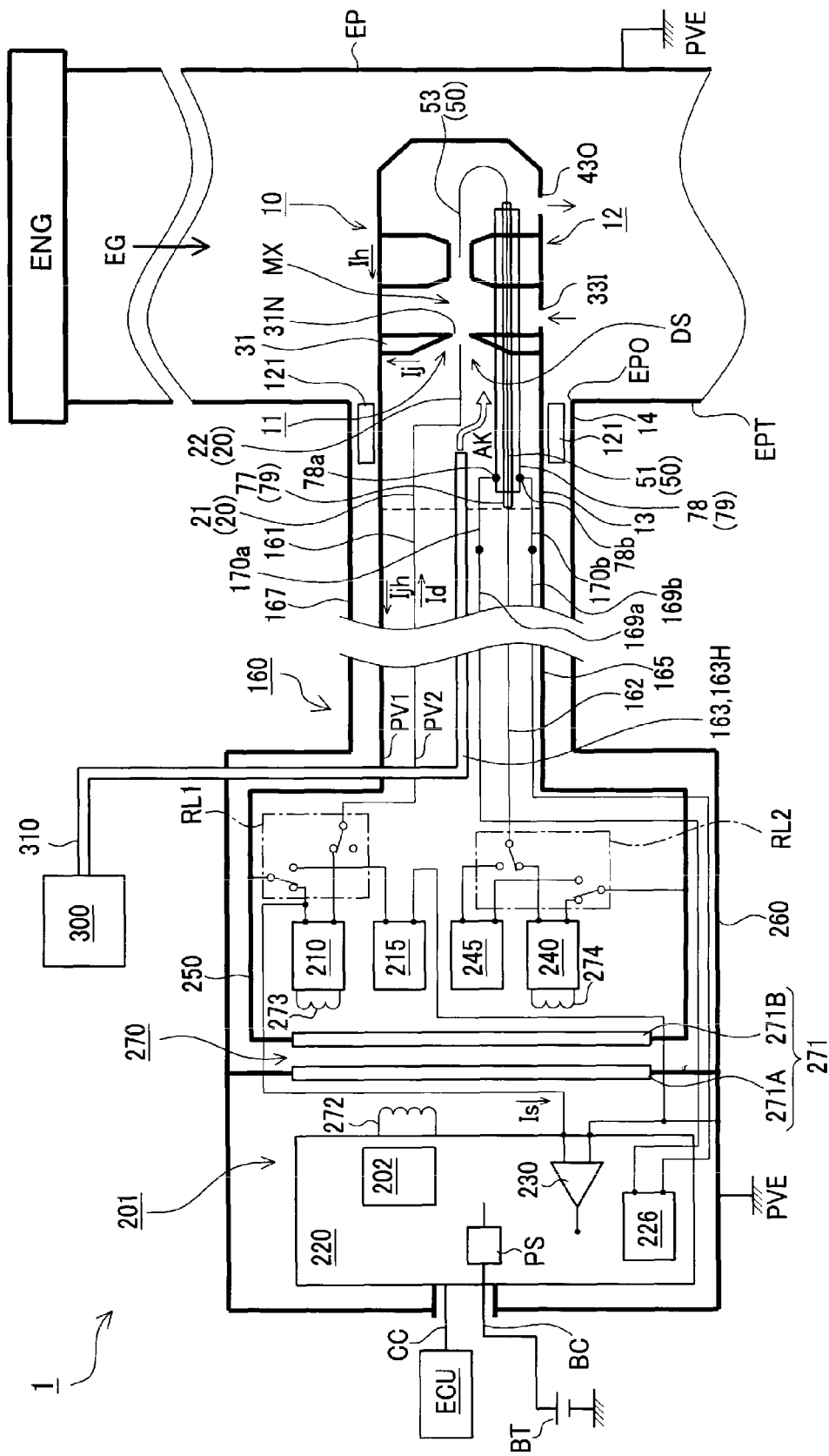
FIG. 2 Explanatory view schematically showing the configuration of the particulate detection system according to the embodiment.
Figure 3:
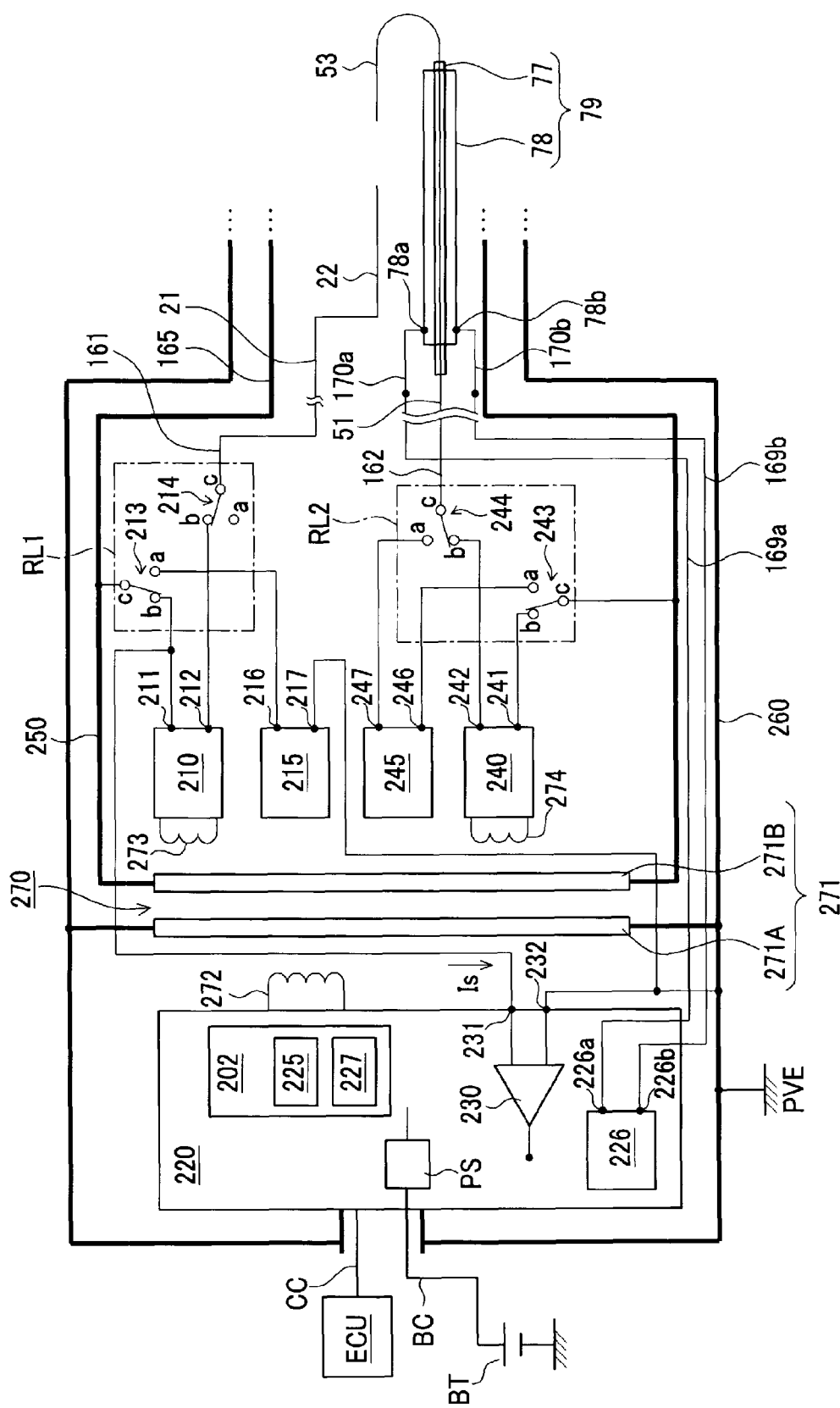
FIG. 3 Explanatory view relating to the embodiment and specifically showing a circuit section of the configuration schematically shown in FIG. 2.

As described above, the circuit section 201 is connected to this cable 160 (see FIG. 2). Specifically, the second output terminal 212 of the ion source power supply circuit 210 is connected to the second potential wiring line 161 via the second switch 214 of the first relay RL1, and is maintained at the second discharge potential PV2 when the ion source power supply circuit 210 is driven. The auxiliary second output terminal 242 of the auxiliary electrode power supply circuit 240 is connected to the auxiliary potential wiring line 162 via the auxiliary second switch 244 of the second relay RL2, and is maintained at the auxiliary electrode potential PV3 when the auxiliary electrode power supply circuit 240 is driven. The first output terminal 211 of the ion source power supply circuit 210 and the signal input terminal 231 of the signal current detection circuit 230 are connected to the inner circuit casing 250 and the first potential wiring line 165 via the first switch 213 of the first relay RL1, and the auxiliary first output terminal 241 of the auxiliary electrode power supply circuit 240 is connected to the inner circuit casing 250 and the first potential wiring line 165 via the auxiliary first switch 243 of the second relay RL2. Thus, these lines are maintained at the first discharge potential PV1 when the ion source power supply circuit 210 is driven. The ground input terminal 232 of the signal current detection circuit 230 is connected, for electrical conduction, to the outer circuit casing 260 and the ground potential wiring line 167, whereby the ground input terminal 232 is maintained at the ground potential PVE.

The first heater energization terminal 226a of the heater energization circuit 226 is connected, for electrical conduction, to the first heater connection wiring line 169a, and the second heater energization terminal 226b of the heater energization circuit 226 is connected, for electrical conduction, to the second heater connection wiring line 169b.

The air feed pipe 310 of the feed pump 300 is extended through the interior of the inner circuit casing 250, and is connected to the air pipe 163 of the cable 160.

Next, the mechanical structure of the present system 1 will be described with reference to FIGS. 4 through 7. Notably, the upper side in FIGS. 4 and 5 will be referred to as the distal end side, and the lower side in FIGS. 4 and 5 will be referred to as the proximal end side. Notably, as to the above-described circuit section 201, description of its mechanical structure is omitted.

First, the detection section 10 will be described (see FIGS. 4 through 7). As described above, the detection section 10 is attached to the mount portion EPT of the exhaust pipe EP (a gas flow pipe) of the engine ENG (an internal combustion engine), the mount portion EPT having the mount opening EPO, and is to come into contact with the exhaust gas EG (a gas under measurement). From the viewpoint of the electrical functions of the detection section 10, the detection section 10 is mainly composed of an ion gas jetting source 11, a particulate electrification section 12, a first communicating member 13, a needlelike electrode member 20, and an auxiliary electrode member 50.

On the distal end side of the cable 160, the second potential wiring line 161, the auxiliary potential wiring line 162, the first heater connection wiring line 169a, and the second heater connection wiring line 169b are passed through an insulating separator 85, and held inside a metallic inner tube 80 together with the separator 85. A distal end portion 163S of the air pipe 163 is opened within the inner tube 80, and an air passage hole 85H at the center of the separator 85 serves as a passage for the compressed air AK released from the air pipe 163.

The inner tube 80 is fitted onto a distal end portion of the cable 160 and is connected, by means of crimping, to the first potential wiring line 165 of the cable 160, which is provided around the inner insulator layer 164 so as to cover it. Therefore, the inner tube 80 electrically communicates with the first potential wiring line 165.

A distal end portion of the second potential wiring line 161 of the cable 160 is connected to an extending portion 21 of the needlelike electrode member 20 inside the separator 85 within the inner tube 80. This needlelike electrode member 20 is formed of tungsten wire, and has the extending portion 21 and a needlelike distal end portion 22. The extending portion 21 generally has the shape of a straight bar. The needlelike distal end portion 22 is located at the distal end (the upper end in the drawings) of the extending portion 21, is formed to have a sharp point like a needle, and serves as a second discharge electrode. The circumference of the extending portion 21 of the needlelike electrode member 20 is covered by a cylindrical tubular, needlelike electrode insulating pipe 75 formed of insulating ceramic such as alumina. The extending portion 21 is passed through a needlelike electrode insertion hole 61H formed in a holding portion 61 of a metallic pipe holder 60, and is held by the holding portion 61 together with the needlelike electrode insulating pipe 75.

A distal end portion of the auxiliary potential wiring line 162 of the cable 160 is connected to an extending portion 51 of the auxiliary electrode member 50 inside the separator 85 within the inner tube 80. The auxiliary electrode member 50 is formed of stainless steel wire, and has the extending portion 51 generally having the shape of a straight bar, a bent portion 52 provided at the distal end of the extending portion 51 and bent back to have a U-like shape, and an auxiliary electrode portion 53 serving as an auxiliary electrode. Notably, a distal end portion of the auxiliary electrode portion 53 is also formed to have a sharp point like a needle. This distal end portion will be referred to as a needlelike distal end portion 53S. The circumference of the extending portion 51 of the auxiliary electrode member 50 is covered by an auxiliary electrode insulating pipe 79 with a heater. The extending portion 51 is passed through an auxiliary electrode insertion hole 61I formed in the holding portion 61 of the pipe holder 60, and is held by the holding portion 61 together with the pipe 79. The heater-equipped auxiliary electrode insulating pipe 79 is composed of a cylindrical tubular, auxiliary electrode insulating pipe 77 formed of insulating ceramic such as alumina, a heater 78 formed on the surface of the auxiliary electrode insulating pipe 77 and united therewith, and an insulating ceramic layer 76 covering them (see FIG. 7).

The heater-equipped auxiliary electrode insulating pipe 79 has two heater terminals 78a and 78b of the heater 78 which are provided on a proximal end portion (a lower portion in FIG. 7) of the insulating pipe 79 to be exposed to the outside. The heater 78 is formed of tungsten, and has heater lead portions 78r1 and 78r2 extending from the heater terminals 78a and 78b toward the distal end side (the upper side in FIG. 7), and two heating portions; i.e., a first heater portion 78h1 located at the distal end and a second heater portion 78h2 located on the proximal end side in relation to the first heater portion 78h1. The first heater portion 78h1 and the second heater portion 78h2 are connected in parallel. These portions are formed on the surface of the auxiliary electrode insulating pipe 77, and the surfaces of these portions are covered with the insulating ceramic layer 76 formed of alumina or the like, whereby the heater-equipped auxiliary electrode insulating pipe 79 is constituted.

The first heater connection wiring line 169a and the second heater connection wiring line 169b of the cable 160 are connected to heater connection terminals 170a and 170b, respectively, inside the separator 85 within the inner tube 80. Within the inner tube 80, the heater connection terminals 170a and 170b extend to a position located on the distal end side of the separator 85, and are connected to the heater terminals 79a and 79b of the heater 78.

As described above, the distal end portion 163S of the air pipe 163 of the cable 160 is opened within the inner tube 80. The pipe holder 60 is fitted into a distal end portion of the inner tube 80. Therefore, the compressed air AK discharged from the air pipe 163 is fed under pressure to a discharge space DS (to be described later) located on the distal end side (the upper side in the drawings) of the air pipe 163 through the air passage hole 85H of the separator 85 and an air passage through hole 61J formed in the holding portion 61 of the pipe holder 60.

Figure 4:
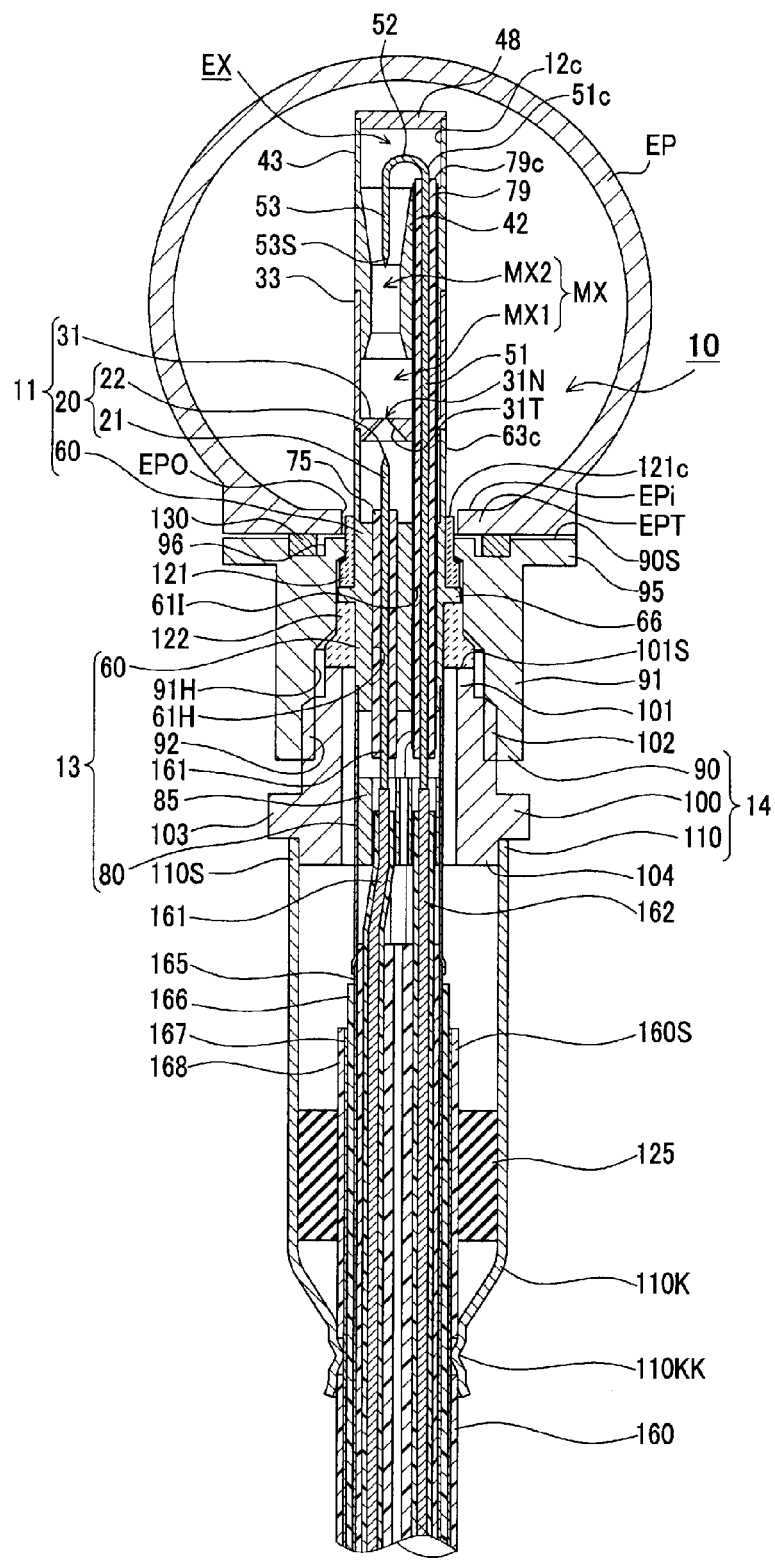
FIG. 4 Vertical sectional view showing the structure of a detection section of the particulate detection system according to the embodiment.
Figure 5:
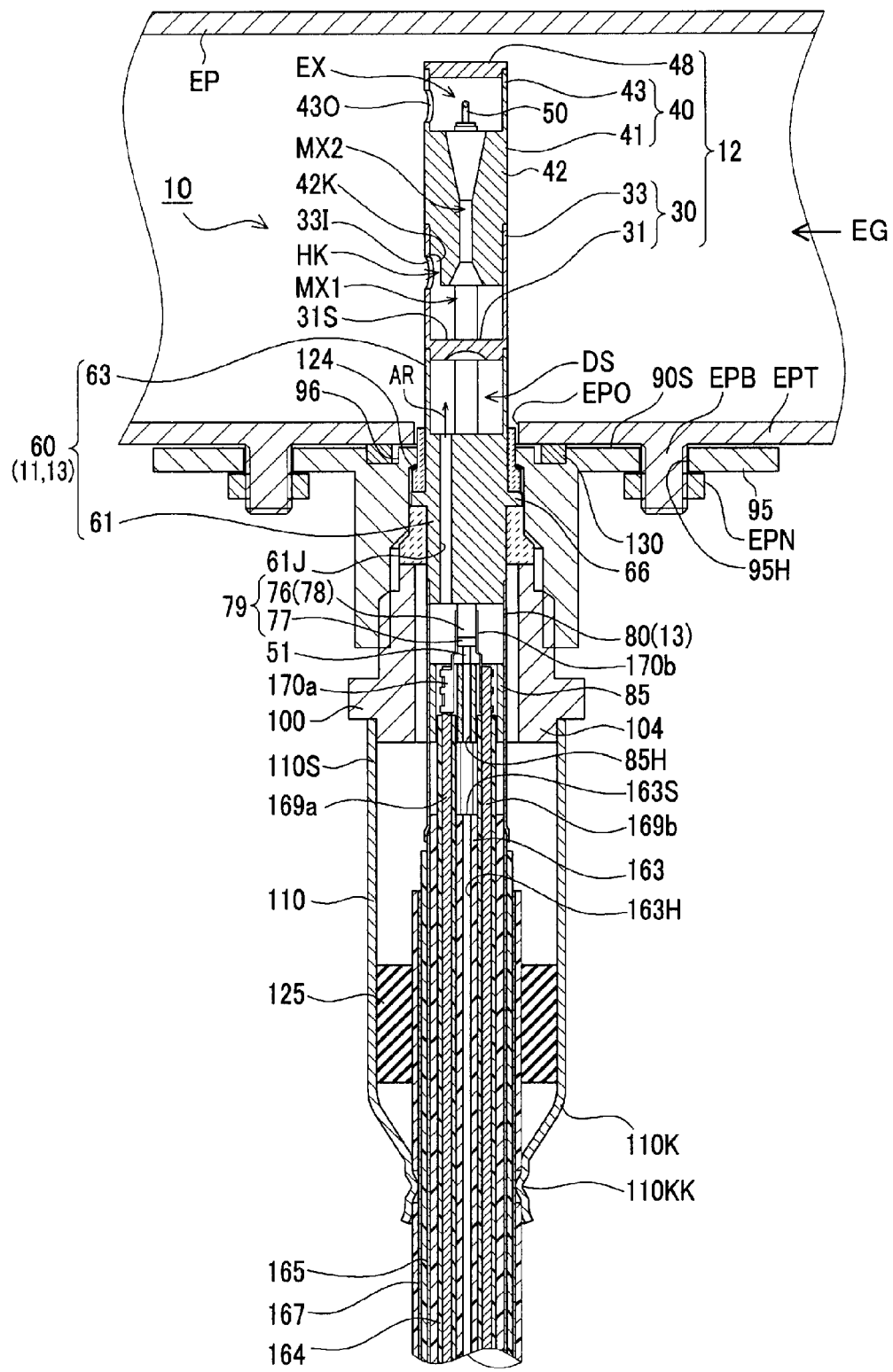
FIG. 5 Vertical cross sectional view at a vertical cross section orthogonal to the cross section of FIG. 4, the vertical cross sectional view showing the structure of the detection section of the particulate detection system according to the embodiment.
Figure 6:
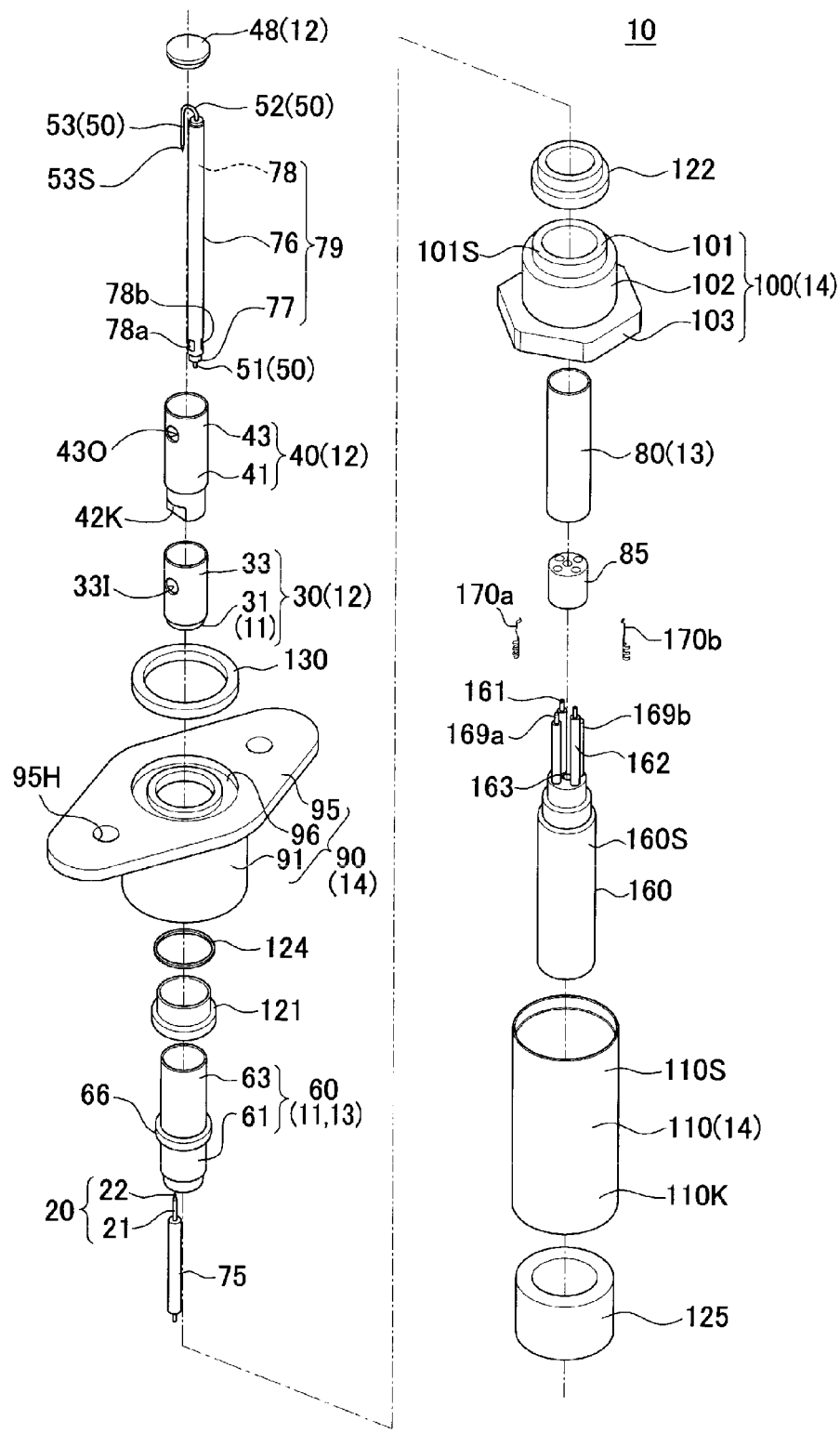
FIG. 6 Exploded perspective view showing the structure of the detection section of the particulate detection system according to the embodiment.
Figure 7:
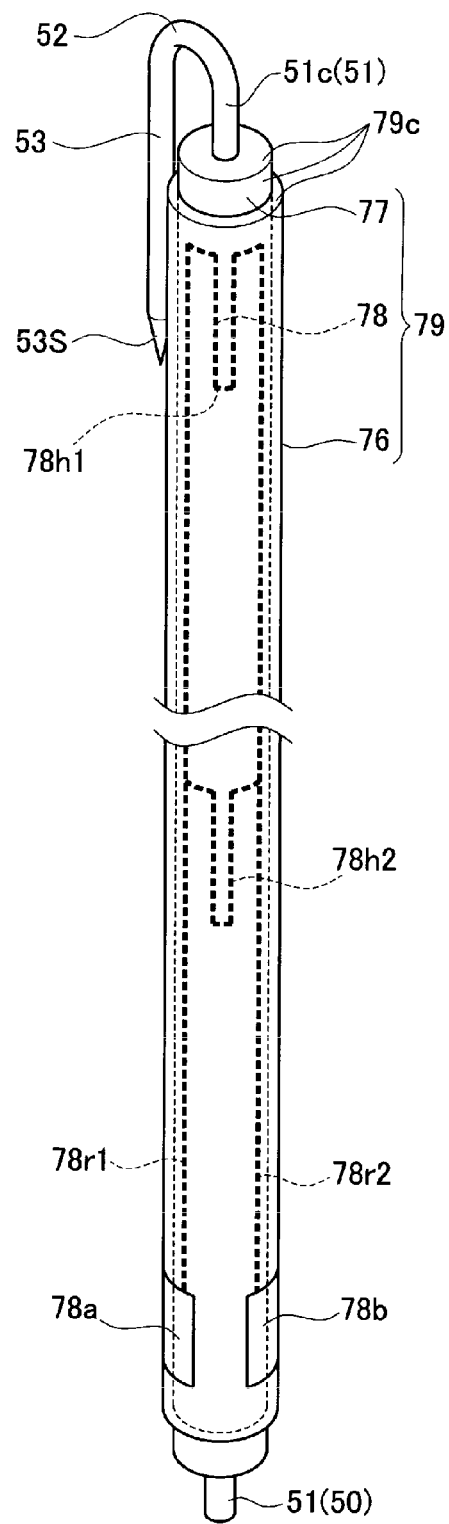
FIG. 7 Enlarged perspective view relating to the embodiment and showing an auxiliary electrode member and an auxiliary electrode insulating pipe with a heater.

The pipe holder 60 shown in FIGS. 4 through 6 is formed of stainless steel, and has the circular columnar, solid holding portion 61, and a cylindrical tubular wall portion 63 extending from the peripheral edge of the holding portion 61 toward the distal end side. The holding portion 61 has an annular holder flange portion 66 bulging radially outward. The holding portion 61 has the needlelike electrode insertion hole 61H, the auxiliary electrode insertion hole 61I, and the air passage through hole 61J, which extend in the vertical direction in the drawings. As described above, the extending portion 21 of the needlelike electrode member 20 is inserted into and is held in the needlelike electrode insertion hole 61H, and the extending portion 51 of the auxiliary electrode member 50 is inserted into and is held in the auxiliary electrode insertion hole 61I. Meanwhile, on the radially inner side of the tubular wall portion 63, the needlelike distal end portion 22 of the needlelike electrode member 20 projects from the holding portion 61 toward the distal end side.

The pipe holder 60 is fitted into the inner tube 80 so that the pipe holder 60 is fixed to the inner tube 80 and electrically communicates with the inner tube 80. The pipe holder 60 and the inner tube 80 form a first communicating member 13 which surrounds the extending portion 21 of the needlelike electrode member 20 and the extending portion 51 of the auxiliary electrode member 50.

Further, a cylindrical tubular nozzle member 30 having a bottom; specifically, a nozzle portion 31 which forms the bottom of the nozzle member 30, is fitted into a distal end portion (an upper portion in the drawings) of the tubular wall portion 63 of the pipe holder 60. This nozzle member 30 is also formed of stainless steel, and has the nozzle portion 31 which is located at the bottom, and a cylindrical tubular wall portion 33 which extends from the peripheral edge of the nozzle portion 31 toward the distal end side. A central portion of the nozzle portion 31 is concaved toward the distal end side, and a fine through hole is formed at the center of the concaved portion. The fine through hole serves as a nozzle 31N. Meanwhile, the tubular wall portion 33 has a single introduction port 331 (see FIG. 5) which is open toward the downstream side of the exhaust pipe EP. As will be described later, the introduction port 331 is an opening for introducing the exhaust gas EG into a mixing region MX (to be described later) formed by the nozzle member 30 and a mixing/exhausting member 40.

The nozzle member 30 is fitted into the pipe holder 60 to thereby be fixed thereto, and electrically communicates with the pipe holder 60. Therefore, the nozzle member 30 is maintained at the first discharge potential PV1.

As a result of the nozzle portion 31 of the nozzle member 30 being fitted into the distal end portion (the upper portion in the drawings) of the tubular wall portion 63 of the pipe holder 60 as described above, the discharge space DS is formed between these members. In the discharge space DS, the needlelike distal end portion 22 of the needlelike electrode member 20 projects from the holding portion 61 of the pipe holder 60, and the needlelike distal end portion 22 faces a facing surface 31T of the nozzle portion 31 which has a concave shape. Accordingly, when a high voltage is applied between the needlelike distal end portion 22 and the nozzle portion 31 (the facing surface 31T), gaseous discharge occurs, whereby $N_2$, $O_2$, etc. in the atmosphere are ionized, whereby positive ions (e.g., $N^{3+}$, $O^{2+}$; hereinafter also referred to as "ions CP") are produced. The compressed air AK is also supplied to the discharge space DS through the air passage through hole 61J of the holding portion 61 of the pipe holder 60. Therefore, air AR originating from the compressed air AK is jetted at high speed from the nozzle 31N of the nozzle portion 31 toward a mixing region MX (which will be described later) located on the distal end side of the nozzle 31N, and the ions CP are also jetted toward the mixing region MX together with the compressed air AK (air AR).

Moreover, the mixing/exhausting member 40 (see FIG. 6) is fitted into a distal end portion (an upper end portion in the drawings) of the tubular wall portion 33 of the nozzle member 30. The mixing/exhausting member 40 is formed of stainless steel, and has a proximal end portion 41 located on the proximal end side (the lower side in the drawings), and a cylindrical distal-end-side tubular wall portion 43 which extends from the peripheral edge of the proximal end portion 41 toward the distal end side. A lid member 48 is attached to the distal end of the distal-end-side tubular wall portion 43 so as to close the tubular wall portion 43. The distal-end-side tubular wall portion 43 has a single exhaust port 430 which is open toward the downstream side of the exhaust pipe EP.

The proximal end portion 41 of the mixing/exhausting member 40 is formed such that the space inside the proximal end portion 41 is narrowed by a capturing electrode 42 which bulges inward, whereby a slit shaped space is formed. Meanwhile, a circular columnar space is formed in the distal-end-side tubular wall portion 43. Notably, the capturing electrode 42 has a cutout 42K at a position corresponding to the position of the introduction port 331 of the nozzle member 30.

The mixing/exhausting member 40 is fitted into the nozzle member 30 to thereby be fixed thereto, and electrically communicates with the nozzle member 30. Therefore, the mixing/exhausting member 40 is maintained at the first discharge potential PV1.

In this manner, an approximately circular columnar space is formed by a distal end surface 31S of the nozzle portion 31 of the nozzle member 30, which surface faces upward in the drawings, the tubular wall portion 33, and the proximal end portion 41 (the capturing electrode 42) of the mixing/exhausting member 40. This space forms a cylindrical columnar mixing region MX1 which is a part of the mixing region MX to be described later. Meanwhile, the slit-shaped internal space defined by the capturing electrode 42 of the proximal end portion 41 of the mixing/exhausting member 40 forms a slit-shaped mixing region MX2. The cylindrical columnar space inside the distal-end-side tubular wall portion 43 forms an exhaust passage EX which communicates with the exhaust port 430. In addition, the cutout 42K of the capturing electrode 42 forms an introduction passage HK which extends from the introduction port 331 to the mixing region MX (the cylindrical columnar mixing region MX1).

Notably, as will be described later, when the air AR containing the ions CP is jetted from the nozzle 31N at high speed, the jetted air AR is exhausted from the exhaust port 430 after passing through the cylindrical columnar mixing region MX1, the slit-shaped mixing region MX2, and the exhaust passage EX. Further, since the air pressure in the circular columnar mixing region MX1 drops due to the flow of the air AR jetted at high speed, the exhaust gas EG located external of the introduction port 331 is taken into the mixing region MX (the circular columnar mixing region MX1, the slit-shaped mixing region MX2) from the intake port 331 through the introduction passage HK. The introduced exhaust gas EGI is mixed with the air AR containing the ions CP in the mixing region MX, and is exhausted together with the air AR from the exhaust port 430 through the exhaust passage EX.

The extending portion 51 of the above-described auxiliary electrode member 50 and the auxiliary electrode insulating pipe 77 surrounding it extend to a position located on the distal end side (the upper side in the drawings) of the pipe holder 60 and the nozzle member 30, and the bent portion 52 which is continuous with the extending portion 51 is located in the distal-end-side tubular wall portion 43 of the mixing/exhausting member 40 (the exhaust passage EX). The auxiliary electrode portion 53 extending toward the proximal end side (the lower side in the drawings) is located in the slit-shaped mixing region MX2 defined by the proximal end portion 41 of the mixing/exhausting member 40.

As shown in FIG. 4, a first insulating spacer 121 which is formed of insulating ceramic such as alumina and which has an approximately cylindrical tubular shape is disposed on the distal end side (the upper side in the drawings) of the holder flange portion 66 of the pipe holder 60. Also, a second insulating spacer 122 which is formed of insulating ceramic such as alumina and which has an approximately cylindrical tubular shape is disposed on the proximal end side (the lower side in the drawings) of the holder flange portion 66. A metallic shell 90 formed of stainless steel is disposed around these spacers to be located outward of these spacers in the radial direction (in the left-right direction in the drawings).

The metallic shell 90 has a tubular portion 91 and a flange portion 95. The approximately cylindrical tubular portion 91 has a holding hole 91H for holding the pipe holder 60, the first insulating spacer 121, and the second insulating spacer 122 therein. A proximal end portion of the tubular portion 91 is a female screw portion 92 having a female screw formed on the inner wall thereof.

Meanwhile, the flange portion 95 is a plate-shaped portion which extends radially outward from a distal end portion of the tubular portion 91 and which has an approximately elliptical outer shape. The flange portion 95 has bolt through holes 95H which penetrate the flange portion 95 in the thickness direction thereof (at two locations in the present embodiment).

A male screw portion 102 of a plug member 100 which has a male screw formed on the outer circumference thereof is in screw engagement with the female screw portion 92 of the tubular portion 91 of the metallic shell 90. The plug member 100 has an approximately cylindrical tubular shape, and surrounds the inner tube 80 without contacting it. On the distal end side (the upper side in the drawings) of the male screw portion 102, the plug member 100 has a flat distal end surface 1015 and a distal end press portion 101 which is smaller in diameter than the male screw portion 102. On the proximal end side (the lower side in the drawings) of the male screw portion 102, the plug member 100 has a hexagonal flange portion 103 which extends radially outward and whose outer circumference has a hexagonal shape.

When the male screw portion 102 of the plug member 100 is screwed into the female screw portion 92 of the metallic shell 90, the plug member 100 moves toward the distal end side, and its distal end press portion 101 presses the second insulating spacer 122 toward the distal end side. As a result, the second insulating spacer 122 presses the holder flange portion 66 of the pipe holder 60 toward the distal end side. Further, the holder flange portion 66 presses the first insulating spacer 121 toward the distal end side. The first insulating spacer 121 engages with the holding hole 91H of the tubular portion 91 of the metallic shell 90 via a sheet packing 124. As a result, the pipe holder 60, the first insulating spacer 121, the second insulating spacer 122, the sheet packing 124, and the plug member 100 are held by the metallic shell 90 to thereby be united together.

The first insulating spacer 121 and the second insulating spacer 122 are present between the pipe holder 60 and the metallic shell 90 so as to separate and insulate them from each other. Notably, a space is provided between the holder flange portion 66 of the pipe holder 60, which bulges radially outward, and the metallic shell 90 (the tubular portion 91) so as to separate and insulate them from each other. Further, when the detection section 10 is attached to the exhaust pipe EP, the first insulating spacer 121 intervenes between the tubular wall portion 63 of the pipe holder 60 and the exhaust pipe EP so as to separate and insulate them from each other.

When the detection section 10 is mounted, as shown in FIG. 5, the nozzle member 30, the mixing/exhausting member 40, etc. are inserted into the exhaust pipe EP through the mounting opening EPO of the mounting portion EPT of the exhaust pipe EP, stud bolts EPB provided adjacent to the mounting opening EPO are passed through the bolt through holes 95H of the flange portion 95, and nuts EPN are attached to the stud bolts EPB for fastening. As a result, the detection section 10, including the metallic shell 90, is fixed to the mounting portion EPT of the exhaust pipe EP.

Notably, a gasket holding groove 96 having an annular shape is formed on a distal end surface 90S of the metallic shell 90 to surround the holding hole 91H, and the metallic shell 90 is airtightly joined to the mounting portion EPT of the exhaust pipe EP via a copper gasket 130 disposed in the gasket holding groove 96.

As a result, the gasket 130, the metallic shell 90, and the plug member 100 are maintained at the ground potential PVE, which is the same potential as that of the exhaust pipe EP.

Further, a cylindrical outer tube 110 formed of stainless steel is connected to a proximal end portion 104 of the plug member 100. This outer tube 110 surrounds the inner tube 80 and a distal end portion 160S of the cable 160 from the radially outer side, and its distal end portion 110S is laser welded to the proximal end portion 104 of the plug member 100 over the entire circumference. A proximal end portion 110K of the outer tube 110 has a reduced outer diameter as compared with the distal end portion thereof, and is fixed to the cable 160 by means of crimping. A crimped portion 110KK of the proximal end portion 110K of the outer tube 110 penetrates the outer insulating cover layer 168, which is the outermost layer of the cable 160, and electrically communicates with the ground potential wiring line 167 located inside the outer insulating cover layer 168. Thus, the outer tube 110 and the ground potential wiring line 167 are maintained at the ground potential PVE, which is the same potential as that of the exhaust pipe EP, through the metallic shell 90, the plug member 100, and the gasket 130, each of which is formed of metal.

Notably, in the present embodiment, in order to prevent the distal end portion 160S of the cable 160 from swinging within the outer tube 110, a cylindrical tubular grommet 125 formed of insulating rubber is disposed between the outer tube 110 and the distal end portion 160S of the cable 160.

Figure 8:
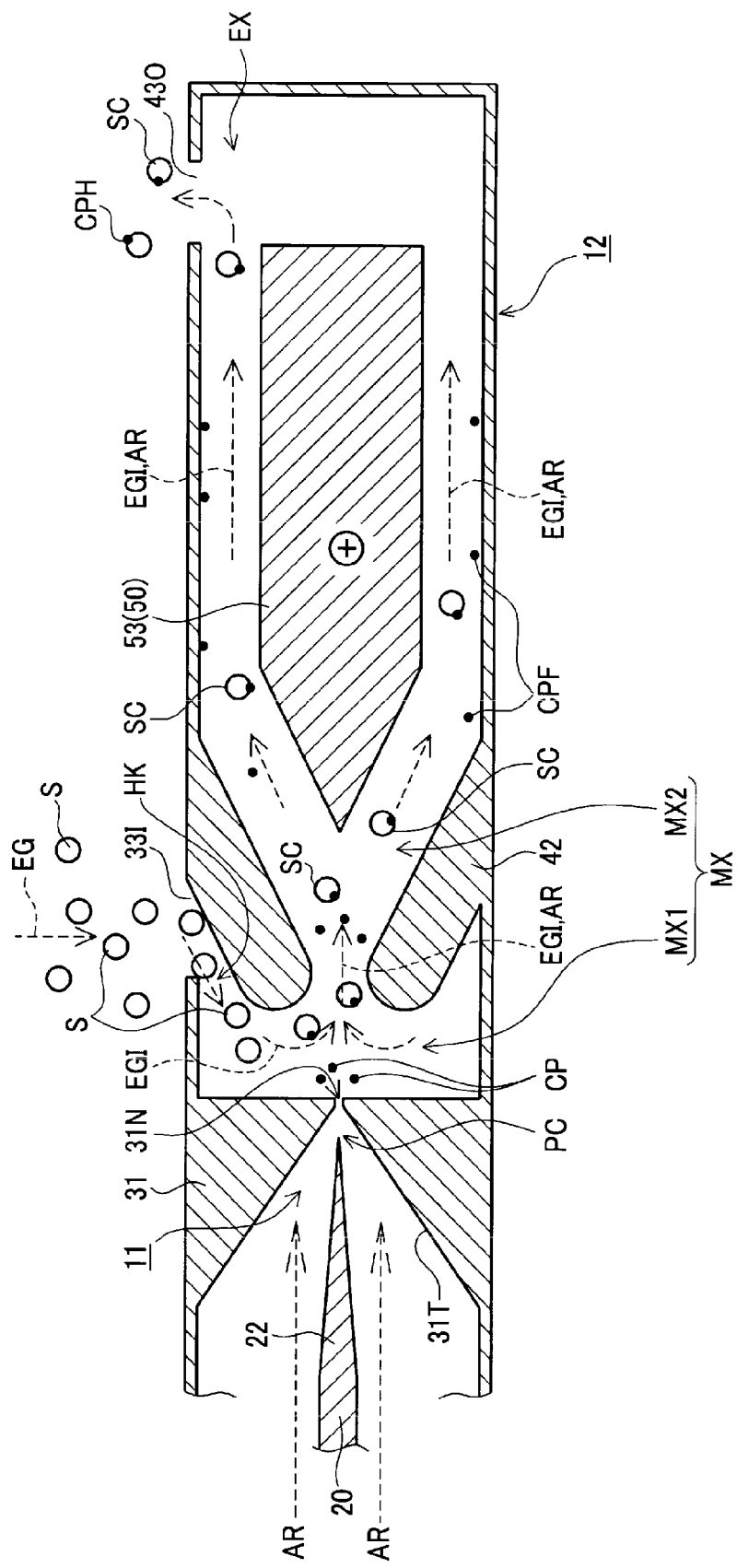
FIG. 8 Explanatory view schematically showing introduction of particulates into a particulate electrification section of the particulate detection system according to the embodiment, electrification of the particulates, and release of the electrified particulates from the particulate electrification section.

Next, the electrical functions and operations of various sections of the particulate detection system 1 of the present embodiment will be described with reference to FIG. 8 in addition to FIGS. 2 through 6. FIG. 8 schematically shows the electrical function and operation of the detection section 10 of the present system 1 in order to facilitate the understanding of the electrical function and operation. It is noted that some portions in FIG. 8 differ in form from those described in other drawings, etc.

The needlelike electrode member 20 is connected, for electrical conduction, with the second output terminal 212 of the ion source power supply circuit 210 via the second potential wiring line 161 of the cable 160. Accordingly, the needlelike electrode member 20 is maintained at the second discharge potential PV2, which is a positive pulse voltage (1 to 2 kV0-p), which is obtained through half-wave rectification of a sinusoidal wave of 100 kHz, in relation to the first discharge potential PV1 as described above.

Also, the auxiliary electrode member 50 is connected, for electrical conduction, with the auxiliary second output terminal 242 of the auxiliary electrode power supply circuit 240 via the auxiliary potential wiring line 162 of the cable 160. Accordingly, the auxiliary electrode member 50 is maintained at the auxiliary electrode potential PV3, which is a positive DC potential of 100 to 200 V in relation to the first potential PV1.

Further, the inner tube 80, the pipe holder 60, the nozzle member 30, and the mixing/exhausting member 40 are connected, for electrical conduction, with the first output terminal 211 of the ion source power supply circuit 210, the auxiliary first output terminal 241 of the auxiliary electrode power supply circuit 240, the inner circuit casing 250 surrounding these circuits, and the signal input terminal 231 of the signal current detection circuit 230 via the first potential wiring line 165 of the cable 160. These are maintained at the first discharge potential PV1.

In addition, the outer tube 110, the plug member 100, the metallic shell 90, and the gasket 130 are connected, for electrical conduction, with the ground input terminal 232 of the signal current detection circuit 230 and the outer circuit casing 260 surrounding the measurement control circuit 220 including the signal current detection circuit 230 via the ground potential wiring line 167 of the cable 160. These are maintained at the ground potential PVE, which is the same as the potential of the exhaust pipe EP.

Accordingly, as described above, gaseous discharge (specifically, corona discharge) occurs between the nozzle portion 31 (the facing surface 31T) maintained at the first discharge potential PV1 and the needlelike distal end portion 22 maintained at the second discharge potential PV2, which is a positive high potential in relation to the first discharge potential PV1. More specifically, positive needle corona PC is produced; i.e., corona is generated around the needlelike distal end portion 22, which serves as a positive electrode. As a result, $N_2$, $O_2$, etc. in the atmospheric air (air) therearound are ionized, whereby positive ions CP are produced. Some produced ions CP pass through the nozzle 31N and are jetted toward the mixing region MX, together with the compressed air AK (air AR) supplied to the discharge space DS.

In the present embodiment, the needlelike distal end portion 22 corresponds to the second discharge electrode, and the nozzle portion 31 of the nozzle member 30 corresponds to the first discharge electrode. Also, the pipe holder 60 (the holding portion 61 and the tubular wall portion 63) and the nozzle portion 31 (the first discharge electrode) of the nozzle member 30, which surround the discharge space DS, and the needlelike distal end portion 22 (the second discharge electrode) constitute an ion source 11 and an ion gas jetting source 11.

When the air AR is jetted to the mixing region MX (the circular columnar mixing region MX1), as described above, the air pressure in the circular columnar mixing region MX1 drops. Therefore, the exhaust gas EG is taken into the mixing region MX (the circular columnar mixing region MX1, the slit-shaped mixing region MX2) from the intake port 331 through the introduction passage HK. The introduced exhaust gas EGI is mixed with the air AR, and is exhausted together with the air AR from the exhaust port 430 through the exhaust passage EX.

At that time, if particulates S such as soot are contained in the exhaust gas EG, as shown in FIG. 8, the particulates S are also introduced into the mixing region MX. Incidentally, the jetted air AR includes ions CP. Therefore, the ions CP adhere to the introduced particulates S such as soot, and the particulates S become positively electrified particulates SC. The positively electrified particulates SC are discharged, together with the air AR, from the exhaust port 430 through the mixing region MX and the exhaust passage EX.

Meanwhile, of the ions CP jetted to the mixing region MX, floating ions CPF not having adhered to the particulates S receive a repulsive force from the auxiliary electrode portion 53 of the auxiliary electrode member 50, and adhere to portions of the mixing/exhausting member 40, which is maintained at the first discharge potential PV1 and which forms the capturing electrode 42. As a result, the floating ions CPF are not exhausted (are captured).

As shown in FIG. 2, when gaseous discharge occurs at the ion gas jetting source 11, a discharge current Id is supplied to the needlelike distal end portion 22 from the second output terminal 212 of the ion source power supply circuit 210. The greater part of the discharge current Id flows to the nozzle portion 31 (received current Ij). This received current Ij flows into the first output terminal 211 of the ion source power supply circuit 210. Meanwhile, a captured current Ih originating from the charge carried by the floating ions CPF captured by the capturing electrode 42 also flows into the first output terminal 211 of the ion source power supply circuit 210. Namely, a received/captured current Ijh (=Ij+Ih) which is the sum of the received current Ij and the captured current Ih flows into the first output terminal 211 of the ion source power supply circuit 210.

However, this received/captured current Ijh is smaller than the discharge current Id by an amount corresponding to the charge of exhausted ions CPH which are exhausted while adhering to the electrified particulates SC. Therefore, a signal current Is corresponding to the difference between the discharge current Id and the received/captured current Ijh (the discharge current Id−the received/captured current Ijh) flows between the first discharge potential PV1 and the ground potential PVE, whereby a balanced state is created.

Accordingly, the amount of particulates S contained in the exhaust gas EG can be detected by detecting, by the signal current detection circuit 230, the signal current Is which corresponds to the amount of charge of the exhausted ions CPH exhausted by the electrified particulates SC.

In the present embodiment, the nozzle member 30, the mixing/exhausting member 40, and the lid member 48, which constitute the mixing region MX and the capturing electrode 42, correspond to the particulate electrifying section 12.

The pipe holder 60 (the holding portion 61 and the tubular wall portion 63) and the inner tube 80 electrically communicate with the above-described particulate electrifying section 12 and the nozzle portion 31 of the nozzle member 30, and surround the extending portion 21 of the needlelike electrode member 20 and the extending portion 51 of the auxiliary electrode member 50. In the present embodiment, the pipe holder 60 (the holding portion 61 and the tubular wall portion 63) and the inner tube 80 correspond to the first communicating member 13. The pipe holder 60 is a portion of the first communicating member 13, and is also a portion of the ion gas jetting source 11 as described above.

The metallic shell 90, the plug member 100, and the outer tube 110 electrically communicate with the exhaust pipe EP and are maintained at the ground potential PVE. Meanwhile, these members are electrically insulated from the particulate electrifying section 12 (the nozzle member 30, etc.) and the first communicating member 13 (the inner tube 80, etc.). Of these members, the tubular portion 91 of the metallic shell 90, the plug member 100, and the outer tube 110 surround portions of the particulate electrifying section 12, the ion gas jetting source 11, and the first communicating member 13, which portions are located on the outer side of the exhaust pipe EP (on the lower side of the exhaust pipe EP in FIGS. 4 and 5). Specifically, they surround a proximal end portion of the extending portion 21 of the needlelike electrode member 20, a proximal end portion of the extending portion 51 of the auxiliary electrode member 50, the holding portion 61 of the pipe holder 60, and the inner tube 80.

In the present embodiment, the metallic shell 90, the plug member 100, and the outer tube 110 correspond to the outer enclosing portion 14.

As described above, the circumference of the extending portion 51 of the auxiliary electrode member 50 is surrounded by the heater-equipped auxiliary electrode insulating pipe 79; specifically, the auxiliary electrode insulating pipe 77, the heater 78 formed on the surface of the auxiliary electrode insulating pipe 77 and united therewith, and the insulating ceramic layer 76 covering them.

A distal end exposed surface 51c of the extending portion 51 of the auxiliary electrode member 50, which surface projects from the distal end of the auxiliary electrode insulating pipe 77 and is located in the particulate electrifying section 12, is in contact with the exhaust gas EG (the gas under measurement). Also, the inner side surface 12c of the particulate electrifying section 12 is in contact with the exhaust gas EG.

Distal-end-side surfaces 79c of the auxiliary electrode insulating pipe 77 of the heater-equipped auxiliary electrode insulating pipe 79 and the insulating ceramic layer 76 covering it are in contact with the exhaust gas EG, and are located between the inner side surface 12c of the particulate electrifying section 12 and the distal end exposed surface 51c of the extending portion 51 of the auxiliary electrode member 50.

The heater-equipped auxiliary electrode insulating pipe 79 is passed through the auxiliary electrode insertion hole 61I formed in the holding portion 61 of the pipe holder 60, and the first insulating spacer 121 is disposed on the radially outer side of a distal end portion of the pipe holder 60. This first insulating spacer 121 intervenes between the pipe holder 60 and the metallic shell 90 so as to electrically insulate them from each other. Inside the exhaust pipe EP, the first insulating spacer 121 intervenes between the tubular wall portion 63 of the pipe holder 60 and the exhaust pipe EP so as to electrically insulate them from each other.

An outer circumferential surface 63c of the tubular wall portion 63 of the pipe holder 60 is in contact with the exhaust gas EG. A distal-end-side surface 121c of the first insulating spacer 121 is located between the outer circumferential surface 63c of the tubular wall portion 63 of the pipe holder 60 and an inner side surface EPi of the exhaust pipe EP.

Namely, the first insulating spacer 121 intervenes between the pipe holder 60 (the first communicating member 13) maintained at the first discharge potential PV1 and the exhaust pipe EP and the metallic shell 90 (the outer enclosing portion 14) maintained at the ground potential PVE so as to electrically insulate them from each other.

The first communicating member 13 including the pipe holder 60 is connected to the terminal c of the first switch 213 of the first relay RL1 through the first potential wiring line 165 of the cable 160 and the inner circuit casing 250. When the coil of the first relay RL1 is energized, electrical continuity is established between the terminals c and a of the first switch 213, whereby the first test terminal 216 of the ground insulation test circuit 215 is connected to the inner circuit casing 250 and the first potential wiring line 165 of the cable 160. The outer enclosing portion 14 including the metallic shell 90 is connected to the ground input terminal 232 of the signal current detection circuit 230 and the second test terminal 217 of the ground insulation test circuit 215 through the ground potential wiring line 167 of the cable 160 and the outer circuit casing 260.

In the system 1 of the present embodiment, the ground insulation test circuit 215 serves as an insulation test means for testing the degree of insulation between the first communicating member 13, and the exhaust pipe EP and the outer enclosing portion 14.

When the tested degree of insulation is high, the drive of the ion gas jetting source 11 and the particulate electrifying section 12 by the ion source power supply circuit 210 is instructed.

Meanwhile, the insulating ceramic layer 76 and the auxiliary electrode insulating pipe 77 of the heater-equipped auxiliary electrode insulating pipe 79 intervene between the particulate electrifying section 12 maintained at the first discharge potential PV1 and the auxiliary electrode member 50 (the extending portion 51 and the auxiliary electrode portion 53) maintained at the auxiliary electrode potential PV3 so as to electrically insulate them from each other.

The particulate electrifying section 12 is connected to the terminal c of the auxiliary first switch 243 of the second relay RL2 through the first communicating member 13, the first potential wiring line 165 of the cable 160, and the inner circuit casing 250. The auxiliary electrode member 50 is connected to the terminal c of the auxiliary second switch 244 of the second relay RL2 through the auxiliary potential wiring line 162 of the cable 160. When the coil of the second relay RL2 is energized, electrical continuity is established between the terminals c and a of the auxiliary first switch 243, whereby the auxiliary first test terminal 246 of the auxiliary electrode insulation test circuit 245 is connected to the first potential wiring line 165 of the cable 160 via the inner circuit casing 250. Also, electrical continuity is established between the terminals c and a of the auxiliary second switch 244, whereby the auxiliary second test terminal 247 of the auxiliary electrode insulation test circuit 245 is connected to the auxiliary potential wiring line 162 of the cable 160.

In the system 1 of the present embodiment, the auxiliary electrode insulation test circuit 245 serves as an insulation test means for testing the degree of insulation between the particulate electrifying section 12 and the first communicating member 13 electrically communicating therewith and the auxiliary electrode member 50 (the extending portion 51 and the auxiliary electrode portion 53). When the tested degree of insulation is high, the drive of the auxiliary electrode member 50 (the auxiliary electrode portion 53) by the auxiliary electrode power supply circuit 240 is instructed.

The heater 78 of the heater-equipped auxiliary electrode insulating pipe 79 is connected to the heater energization circuit 226. The system 1 of the present embodiment includes insulation recovery energization instruction means, operable when the degree of insulation tested by the above-mentioned insulation test means is low, for instructing the heater energization circuit 226 to energize the heater 78 to thereby heat the first insulating spacer 121 (the distal-end-side surface 121c) and the heater-equipped auxiliary electrode insulating pipe 79 (the distal-end-side surface 79c). As a result, the insulating performance of the first insulating spacer 121 and the insulating performances of the auxiliary electrode insulating pipe 77 and the insulating ceramic layer 76 of the heater-equipped auxiliary electrode insulating pipe 79 are recovered.

Figure 9:
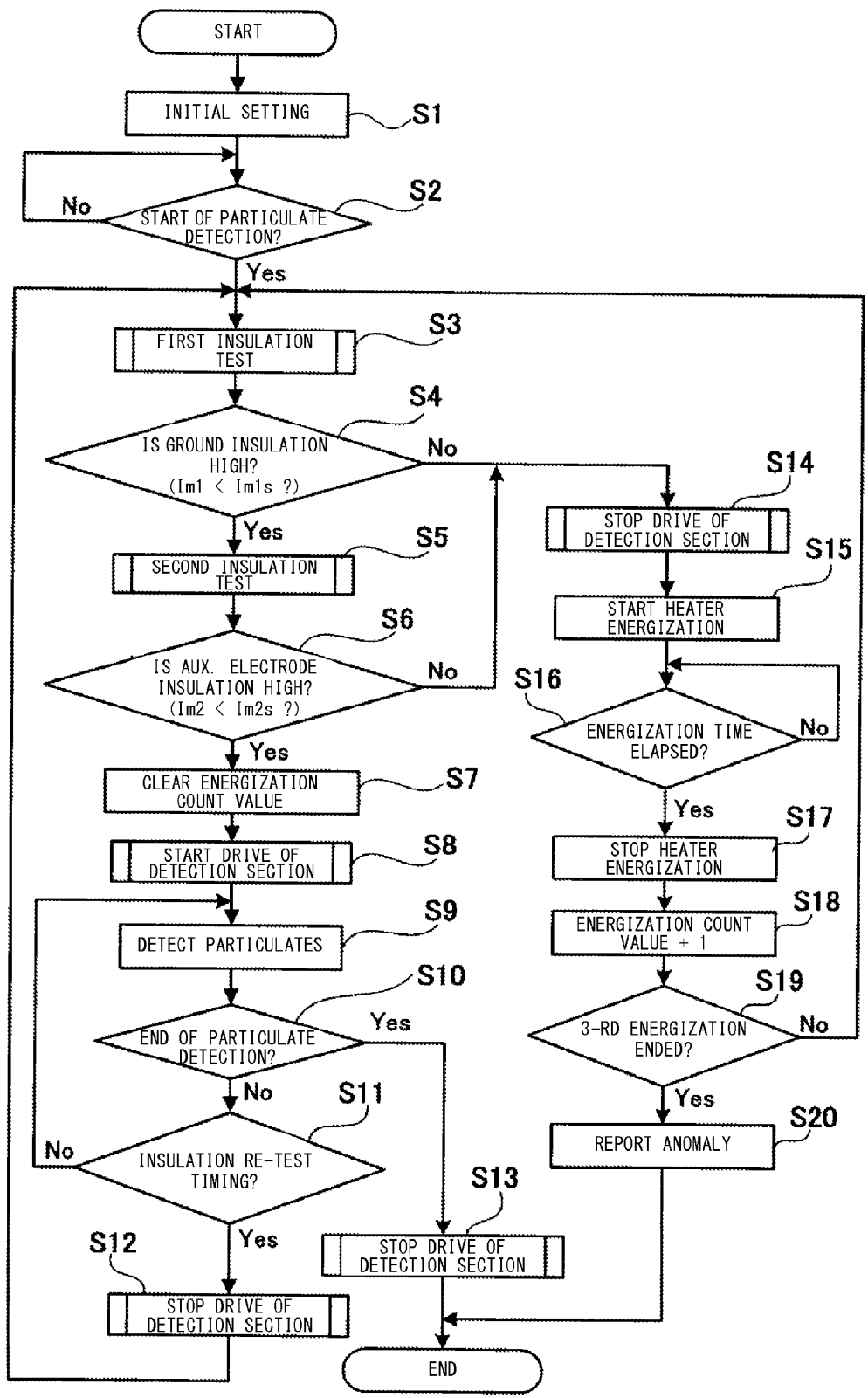
FIG. 9 Flowchart showing operation of the particulate detection system according to the embodiment.

Operation of the microprocessor 202 of the present system 1 which executes a particulate detection routine will be described with reference to the flowchart of FIG. 9.

When a key switch (not shown) of the engine ENG is turned on, the particulate detection system 1 (the microprocessor 202 of the measurement control circuit 220) is started. At step S1, the microprocessor 202 performs necessary initial setting. In step S2 subsequent thereto, the microprocessor 202 determines whether or not the start of the particulate detection is instructed by the ECU.

When the start of particulate detection is not instructed (No), the microprocessor 202 repeats step S2 so as to wait until the start of particulate detection is instructed by the ECU. When the start of the particulate detection is instructed (Yes), the microprocessor 202 proceeds to step S3.

In step S3, the microprocessor 202 executes a first insulation test subroutine (to be described later) for testing the degree of insulation between the first communicating member 13 (the first potential member), and the exhaust pipe EP and the outer enclosing portion 14 (the ground potential member).

Next, in step S4, the microprocessor 202 determines whether or not the degree of insulation tested by the first insulation test of step S3 is high by determining whether or not a leak current Im1 is smaller than a reference value Im1s. When the degree of insulation is low (No), the microprocessor 202 proceeds to step S14. When the degree of insulation is high (Yes), the microprocessor 202 proceeds to step S5.

In step S5, the microprocessor 202 executes a second insulation test subroutine (to be described later) for testing the degree of insulation between the particulate electrifying section 12 (the first potential member) and the auxiliary electrode member 50 (the auxiliary electrode portion 53 and the extending portion 51).

Next, in step S6, the microprocessor 202 determines whether or not the degree of insulation tested by the second insulation test of step S5 is high by determining whether or not a leak current Im2 is smaller than a reference value Im2s. When the degree of insulation is low (No), the microprocessor 202 proceeds to step S14. When the degree of insulation is high (Yes), the microprocessor 202 proceeds to step S7.

Namely, only when both the degree of insulation tested by the first insulation test of step S3 and the degree of insulation tested by the second insulation test of step S5 are high, the microprocessor 202 proceeds to step S7, and in other cases, the microprocessor 202 proceeds to step S14.

In step S7, the microprocessor 202 clears an energization count value, which will be described later. In step S8 subsequent thereto, the microprocessor 202 executes a detection section drive start subroutine (to be described) to thereby start the drive of the ion gas jetting source 11 and the particulate electrifying section 12 by the ion source power supply circuit 210 and the drive of the auxiliary electrode portion 53 of the auxiliary electrode member 50 by the auxiliary electrode power supply circuit 240.

After that, in step S9, the microprocessor 202 performs the particulate detection by detecting the signal current Is by using the signal current detection circuit 230.

When the particulate detection of step S9 is completed, in step S10 subsequent thereto, the microprocessor 202 determines whether or not the end of particulate detection is instructed by the ECU. When the end of particulate detection is not instructed (No), the microprocessor 202 proceeds to step S11 and determines whether or not the timing of re-testing the degree of insulation has come. When the microprocessor 202 determines in step S11 that the timing of re-testing the degree of insulation has not yet come (No), the microprocessor 202 returns to step S9 and repeats the particulate detection.

Meanwhile, when the end of particulate detection is instructed in step S10 (Yes), the microprocessor 202 proceeds to step S13 and executes a detection section drive stop subroutine, which will be described later, to thereby stop the drive of the ion source power supply circuit 210 and the auxiliary electrode power supply circuit 240. The microprocessor 202 then ends the processing of the present particulate detection routine.

When the microprocessor 202 determines in step S11 that the timing of re-testing the degree of insulation has come (Yes), the microprocessor 202 proceeds to step S12, and executes a detection section drive stop subroutine which is identical to the detection section drive stop subroutine of step S13 to thereby stop the drive of the ion source power supply circuit 210 and the auxiliary electrode power supply circuit 240. Subsequently, the microprocessor 202 returns to step S3 and resumes the test of insulating performance.

Figure 13:
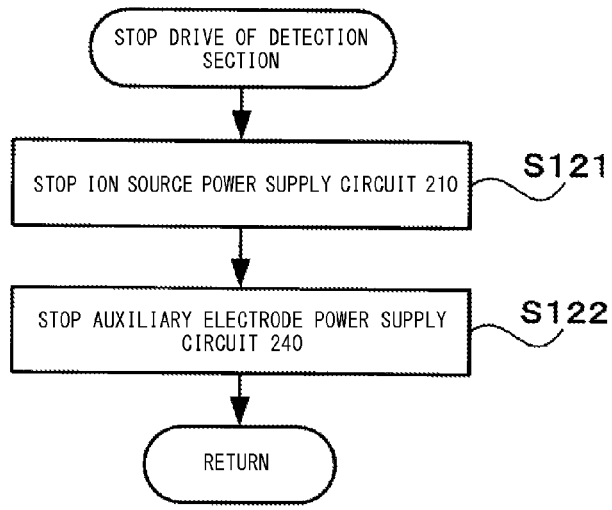
FIG. 13 Flowchart showing the details of a detection section drive stop subroutine.

Here, the detection section drive stop subroutine performed in step S12 and step S13 will be described with reference to the flowchart of FIG. 13.

First, in step S121, the microprocessor 202 stops the drive of the ion source power supply circuit 210 to thereby stop the drive of the ion gas jetting source 11 and the particulate electrifying section 12. Next, in step S122, the microprocessor 202 stops the drive of the auxiliary electrode power supply circuit 240 to thereby stop the drive of the auxiliary electrode portion 53 of the auxiliary electrode member 50. The microprocessor 202 then ends the subroutine.

Meanwhile, even in the case where the microprocessor 202 proceeds to step S14 from step S4 or step S6, the microprocessor 202 executes the above-described detection section drive stop subroutine (which is the same as the detection section drive stop subroutine performed in step S12 and step S13) to thereby stop the drive of the ion gas jetting source 11 and the particulate electrifying section 12 by the ion source power supply circuit 210 and the drive of the auxiliary electrode portion 53 of the auxiliary electrode member 50 by the auxiliary electrode power supply circuit 240. In general, in the case where this step S14 is executed, the drive of the ion source power supply circuit 210 and the auxiliary electrode power supply circuit 240 by step S8 is not performed. However, by executing the detection section drive stop subroutine in step S14, it becomes possible to reliably prevent occurrence of problems such as failures of the ion source power supply circuit 210 and the auxiliary electrode power supply circuit 240 themselves or a failure of the detection section 10, in the case where the tested degree of insulation (insulating performance) is low, including the case where some anomaly occurs.

Next, in step S15, the microprocessor 202 starts the energization of the heater 78 by the heater energization circuit 226. After that, in step S16, the microprocessor 202 determines whether or not a prescribed energization time has elapsed after the start of the energization of the heater 78. When the prescribed energization time has not yet elapsed (No), the microprocessor 202 repeats step S16. When the prescribed energization time has elapsed (Yes), the microprocessor 202 proceeds to step S17, and stops the energization of the heater 78 by the heater energization circuit 226.

As a result, the first insulating spacer 121 (the distal-end-side surface 121c) and the heater-equipped auxiliary electrode insulating pipe 79 (the distal-end-side surface 79c) are heated, whereby foreign substances such as water and soot are removed. Thus, the insulating performance of the first insulating spacer 121 and the insulating performances of the auxiliary electrode insulating pipe 77 and the insulating ceramic layer 76 of the heater-equipped auxiliary electrode insulating pipe 79 are recovered.

In step S18, the microprocessor 202 increases, by one, the energization count value used for counting the number of times of energization of the heater 78 by the heater energization circuit 226. In step S19 subsequent thereto, the microprocessor 202 determines, on the basis of this energization count value, whether or not the third energization of the heater 78 by the heater energization circuit 226 has ended. In the case where the energization of the heater 78 has not yet repeated three times (No), the microprocessor 202 returns to step S3, and again executes the particulate detection routine, starting from the test of insulating performance. Meanwhile, in the case where the energization of the heater 78 has repeated three times (Yes), the microprocessor 202 proceeds to step S20, and reports occurrence of an anomaly. After that, the microprocessor 202 ends the processing of the present particulate detection routine. Occurrence of an anomaly is reported, because in the case where the insulating performance does not recover even after heating is performed three times, it is considered that the detection section 10 is in an anomalous state.

Figure 10:
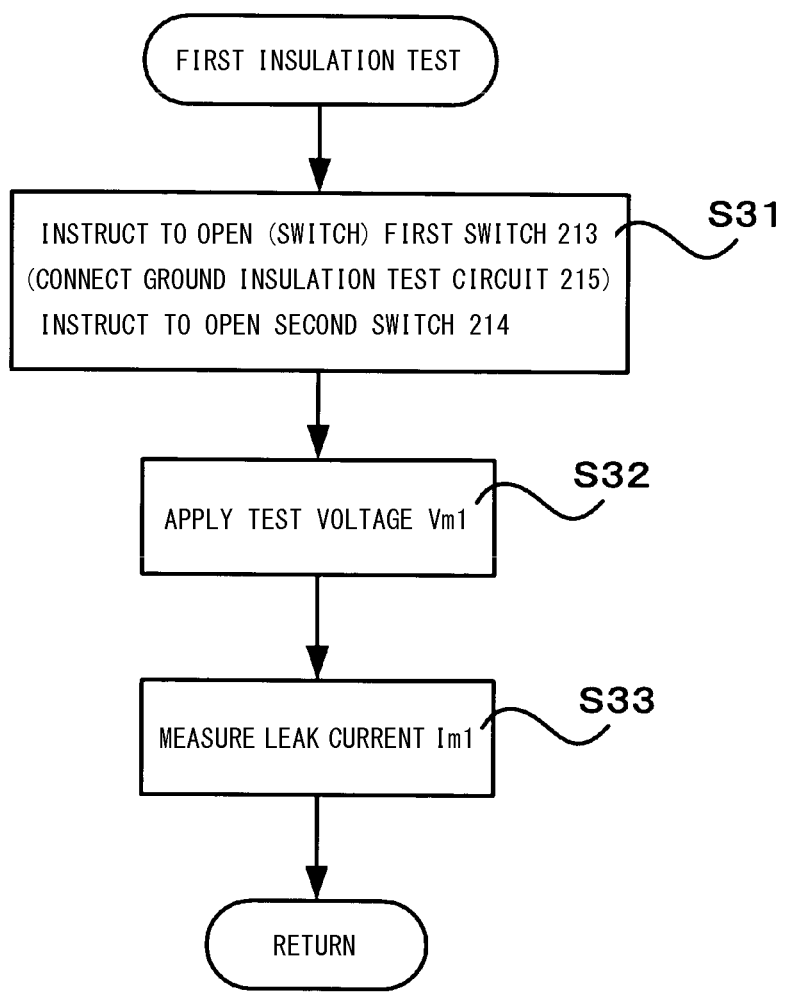
FIG. 10 Flowchart showing the details of a first insulation test subroutine.

Next, the first insulation test subroutine performed in step S3 will be described with reference to the flowchart of FIG. 10.

In step S31, the microprocessor 202 issues an instruction for breaking (switching) the circuit between the first output terminal 211 of the ion source power supply circuit 210 and the first communicating member 13 by the first switch 213. At the same time, the ground insulation test circuit 215 is connected to the first communicating member 13. Also, the microprocessor 202 issues an instruction for breaking the circuit between the second output terminal 212 of the ion source power supply circuit 210 and the needlelike electrode member 20 (the extending portion 21) by the second switch 214.

Specifically, as a result of energization of the coil of the first relay RL1, the electrical continuity between the terminals c and b of the first switch 213 is broken (the circuit between the terminals c and b is opened) and the electrical continuity between the terminals c and a of the first switch 213 is established. As a result, the first output terminal 211 of the ion source power supply circuit 210 and the signal input terminal 231 of the signal current detection circuit 230 are disconnected from the first potential wiring line 165 of the cable 160 and the first communicating member 13 electrically communicating with the first potential wiring line 165. Meanwhile, the first test terminal 216 of the ground insulation test circuit 215 is connected to the first potential wiring line 165 of the cable 160 and the first communicating member 13. Also, the electrical continuity between the terminals c and b of the second switch 214 is broken (the circuit between the terminals c and b is opened), whereby the second output terminal 212 of the ion source power supply circuit 210 is disconnected from the second potential wiring line 161 of the cable 160 and the needlelike electrode member 20 electrically communicating with the second potential wiring line 161.

Next, in step S32, the microprocessor 202 applies a test voltage Vm1 between the first test terminal 216 of the ground insulation test circuit 215 electrically communicating with the first communicating member 13 and the second test terminal 217 maintained at the ground potential PVE.

Subsequently, in step S33, the microprocessor 202 measures the leak current Im1 which flows between the first and second test terminals 216 and 217 of the ground insulation test circuit 215; i.e., between the first communicating member 13 and the exhaust pipe EP or the outer enclosing portion 14 maintained at the ground potential PVE. The microprocessor 202 then ends the present subroutine.

Figure 11:
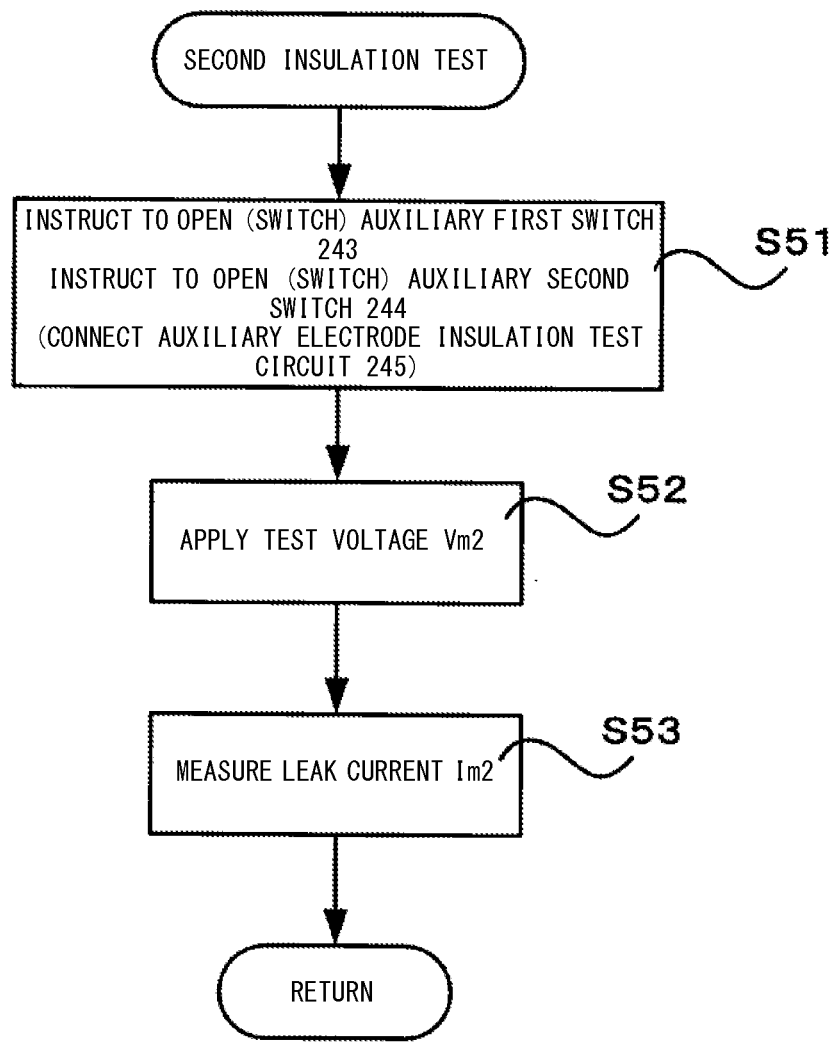
FIG. 11 Flowchart showing the details of a second insulation test subroutine.

Next, the second insulation test subroutine performed in step S5 will be described with reference to the flowchart of FIG. 11.

In step S51, the microprocessor 202 issues an instruction for breaking (switching) the circuit between the auxiliary electrode first output terminal 241 of the auxiliary electrode power supply circuit 240 and the first communicating member 13 by the auxiliary first switch 243. The microprocessor 202 also issues an instruction for breaking (switching) the circuit between the auxiliary second output terminal 242 of the auxiliary electrode power supply circuit 240 and the auxiliary electrode member 50 (the extending portion 51) by the auxiliary second switch 244. At the same time, the auxiliary electrode insulation test circuit 245 is connected to the first communicating member 13 and the auxiliary electrode member 50.

Specifically, as a result of energization of the coil of the second relay RL2, the electrical continuity between the terminals c and b of the auxiliary first switch 243 is broken (the circuit between the terminals c and b is opened) and the electrical continuity between the terminals c and a of the auxiliary first switch 243 is established. As a result, the auxiliary first output terminal 241 of the auxiliary electrode power supply circuit 240 is disconnected from the first potential wiring line 165 of the cable 160 and from the first communicating member 13 and the particulate electrifying section 12 which electrically communicate with the first potential wiring line 165. Meanwhile, the auxiliary first test terminal 246 of the auxiliary electrode insulation test circuit 245 is connected to the first potential wiring line 165 of the cable 160, the first communicating member 13, and the particulate electrifying section 12. Also, the electrical continuity between the terminals c and b of the auxiliary second switch 244 is broken (the circuit between the terminals c and b is opened) and the electrical continuity between the terminals c and a of the auxiliary second switch 244 is established. As a result, the auxiliary second output terminal 242 of the auxiliary electrode power supply circuit 240 is disconnected from the auxiliary potential wiring line 162 of the cable 160 and the auxiliary electrode member 50 electrically communicating with the auxiliary potential wiring line 162. Meanwhile, the auxiliary second test terminal 247 of the auxiliary electrode insulation test circuit 245 are connected to the auxiliary potential wiring line 162 of the cable 160 and the auxiliary electrode member 50.

Next, in step S52, the microprocessor 202 applies a test voltage Vm2 between the auxiliary first test terminal 246 of the auxiliary electrode insulation test circuit 245, which electrically communicates with the first communicating member 13 and the particulate electrifying section 12, and the auxiliary second test terminal 247 electrically communicating with the auxiliary electrode member 50.

Subsequently, in step S53, the microprocessor 202 measures the leak current Im2 which flows between the auxiliary first and second test terminals 246 and 247 of the auxiliary electrode insulation test circuit 245; i.e., between the first communicating member 13 and the particulate electrifying section 12, and the auxiliary electrode member 50 (the extending portion 51 and the auxiliary electrode portion 53). The microprocessor 202 then ends the present subroutine.

Figure 12:
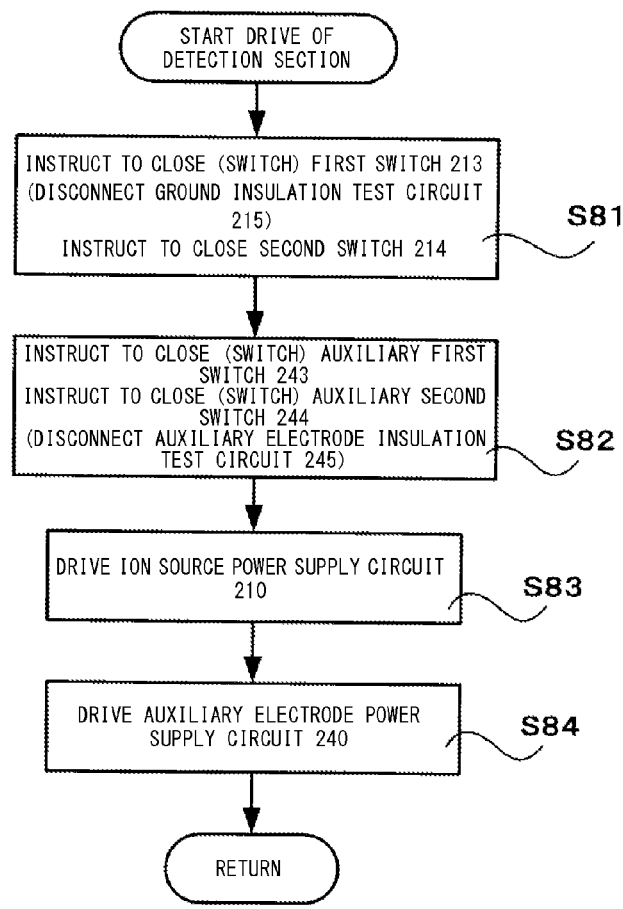
FIG. 12 Flowchart showing the details of a detection section drive start subroutine.

Next, the detection section drive start subroutine performed in step S8 will be described with reference to the flowchart of FIG. 12.

In step S81, the microprocessor 202 issues an instruction for closing (switching) the circuit between the first output terminal 211 of the ion source power supply circuit 210 and the first communicating member 13 by the first switch 213. At the same time, the ground insulation test circuit 215 is disconnected from the first communicating member 13. The microprocessor 202 also issues an instruction for closing (switching) the circuit between the second output terminal 212 of the ion source power supply circuit 210 and the needlelike electrode member 20 (the extending portion 21) by the second switch 214.

Specifically, as a result of de-energization of the coil of the first relay RL1, the electrical continuity between the terminals c and a of the first switch 213 is broken, and the electrical continuity between the terminals c and b of the first switch 213 is established (the circuit between the terminals c and b is closed). As a result, the first test terminal 216 of the ground insulation test circuit 215 is disconnected from the first potential wiring line 165 of the cable 160 and the first communicating member 13 electrically communicating with the first potential wiring line 165, and the first output terminal 211 of the ion source power supply circuit 210 and the signal input terminal 231 of the signal current detection circuit 230 are connected to the first potential wiring line 165 of the cable 160 and the first communicating member 13. Also, the electrical continuity between the terminals c and b of the second switch 214 is established (the circuit between the terminals c and b is closed), whereby the second output terminal 212 of the ion source power supply circuit 210 is connected to the second potential wiring line 161 of the cable 160 and the needlelike electrode member 20 electrically communicating with the second potential wiring line 161.

Next, in step S82, the microprocessor 202 issues an instruction for closing (switching) the circuit between the auxiliary first output terminal 241 of the auxiliary electrode power supply circuit 240 and the first communicating member 13 by the auxiliary first switch 243. The microprocessor 202 also issues an instruction for closing (switching) the circuit between the auxiliary second output terminal 242 of the auxiliary electrode power supply circuit 240 and the auxiliary electrode member 50 (the extending portion 51) by the auxiliary second switch 244. At the same time, the auxiliary electrode insulation test circuit 245 is disconnected from the first communicating member 13 and the auxiliary electrode member 50.

Specifically, as a result of de-energization of the coil of the second relay RL2, the electrical continuity between the terminals c and a of the auxiliary first switch 243 is broken and the electrical continuity between the terminals c and b of the auxiliary first switch 243 is established (the circuit between the terminals c and b is closed). As a result, the auxiliary first test terminal 246 of the auxiliary electrode insulation test circuit 245 is disconnected from the first potential wiring line 165 of the cable 160 and from the first communicating member 13 and the particulate electrifying section 12 which electrically communicate with the first potential wiring line 165. Meanwhile, the auxiliary first output terminal 241 of the auxiliary electrode power supply circuit 240 are connected to the first potential wiring line 165 of the cable 160, the first communicating member 13, and the particulate electrifying section 12. Also, the electrical continuity between the terminals c and a of the auxiliary second switch 244 is broken, and the electrical continuity between the terminals c and b of the auxiliary second switch 244 is established (the circuit between the terminals c and b is closed). As a result, the auxiliary second test terminal 247 of the auxiliary electrode insulation test circuit 245 is disconnected from the auxiliary potential wiring line 162 of the cable 160 and from the auxiliary electrode member 50 electrically communicating with the auxiliary potential wiring line 162. Meanwhile, the auxiliary second output terminal 242 of the auxiliary electrode power supply circuit 240 are connected to the auxiliary potential wiring line 162 of the cable 160 and the auxiliary electrode member 50.

Next, in step S83, the microprocessor 202 starts the drive of the ion source power supply circuit 210 so as to apply the first discharge potential PV1 to the ion gas jetting source 11 and the particulate electrifying section 12 and apply the second discharge potential PV2 to the needlelike distal end portion 22 of the needlelike electrode member 20. Subsequently, in step S84, the microprocessor 202 starts the drive of the auxiliary electrode power supply circuit 240 so as to apply the auxiliary electrode potential PV3 to the auxiliary electrode portion 53 of the auxiliary electrode member 50. After having started the drive of the ion source power supply circuit 210 and the auxiliary electrode power supply circuit 240, the microprocessor 202 ends the present subroutine, and proceeds to step S9 so as to perform the particulate detection.

In the above-described manner, the microprocessor 202 performs the particulate detection, and also performs the first insulation test and the second insulation test before the particulate detection. When the degree of insulation (insulating performance) is low, the microprocessor 202 energizes the heater 78 to thereby recover the insulating performance.

In the present embodiment, the microprocessor 202 of the measurement control circuit 220 corresponds to the drive control section 225 which controls the ion source power supply circuit 210 and the auxiliary electrode power supply circuit 240, and to the heater energization control section 227 which controls the heater energization circuit 226. The ground insulation test circuit 215 and the microprocessor 202 which executes step S3 (the first insulation test) correspond to the insulation test means for testing the degree of insulation between the first communicating member 13 (the first potential member), and the exhaust pipe EP and the outer enclosing portion 14 (the ground potential member). The auxiliary electrode insulation test circuit 245 and the microprocessor 202 which executes step S5 (the second insulation test) correspond to the insulation test means for testing the degree of insulation between the particulate electrifying section 12 (the first potential member) and the auxiliary electrode member 50 (the auxiliary electrode portion 53 and the extending portion 51).

The microprocessor 202 which executes steps S4 and S6 corresponds to the drive permission/prohibition determination means. The microprocessor 202 which executes step S14 corresponds to the drive stop means. The microprocessor 202 which executes steps S15 to S17 corresponds to the insulation recovery energization instruction means.

The microprocessor 202 which executes step S81 corresponds to the drive-time switch closing instruction means. The microprocessor 202 which executes step S31 corresponds to the test-time switch opening instruction means.

The microprocessor 202 which executes step S82 corresponds to the drive-time auxiliary switch closing instruction means. The microprocessor 202 which executes step S51 corresponds to the test-time auxiliary switch opening instruction means.

As described above, in the system 1 of the present embodiment, the degree of insulation between the first communicating member 13 (the first potential member), and the gas flow pipe EP and the outer enclosing portion 14 (the ground potential member) is tested by the insulation test means (the first insulation test). The drive permission/prohibition determination means determines, on the basis of the degree of insulation, whether to permit the drive of the ion gas jetting source 11 and the particulate electrifying section 12 by the ion source power supply circuit 210. Therefore, the amount of particulates S can be detected properly. Also, failure of the ion source power supply circuit 210 can be prevented.

In the system 1 of the present embodiment, the first switch 213 is provided between the first output terminal 211 of the ion source power supply circuit 210 and the first communicating member 13, and the second switch 214 is provided between the second output terminal 212 and the extending portion 21 of the needlelike electrode member 20. When the detection section 10 is driven, these switches are closed. Therefore, the detection section 10 (the ion gas jetting source 11 and the particulate electrifying section 12) can be driven by the ion source power supply circuit 210. Meanwhile, when the degree of insulation between the first communicating member 13 (the first potential member), and the gas flow pipe EP and the outer enclosing portion 14 (the ground potential member) is tested, the first switch 213 and the second switch 214 are opened. As a result, the ion source power supply circuit 210 is disconnected. Therefore, the ion source power supply circuit 210 can be protected from the test voltage Vm1 which is applied when the degree of insulation (insulating performance) is tested. In addition, the degree of insulation between the first communicating member 13 (the first potential member), and the gas flow pipe EP and the outer enclosing portion 14 (the ground potential member) can be tested properly without being affected by the ion source power supply circuit 210.

Notably, as to the tubular wall portion 63 of the pipe holder 60, the exhaust pipe EP, and the first insulating spacer 121 within the exhaust pipe EP, which are a portion of the members used in the present embodiment, the first discharge potential PV1, which is the potential of the first communicating member 13 including the pipe holder 60, corresponds to the first potential in the present invention. The ground potential PVE, which is the potential of the exhaust pipe EP and the outer enclosing portion 14, corresponds to the second potential in the present invention. The ion source power supply circuit 210 corresponds to the drive circuit and the ion source drive circuit in the present invention.

The first discharge electrode 31 of the ion gas jetting source 11, the particulate electrifying section 12, and the first communicating member 13 correspond to the first potential member, and the outer enclosing portion 14 corresponds to the second potential member and the ground potential member. The extending portion 21 of the needlelike electrode member 20 corresponds to the second discharge electrode communicating member.

The first insulating spacer 121 corresponds to the insulating member.

Moreover, in the system 1 of the present embodiment, the degree of insulation between the first discharge electrode 31 of the ion source 11 and the particulate electrifying section 12 (the first potential member), and the auxiliary electrode portion 53 and the extending portion 51 (auxiliary potential member) of the auxiliary electrode member 50 is tested by the insulation test means (the second insulation test). The drive permission/prohibition determination means determines, on the basis of the degree of insulation, whether to permit the drive of the auxiliary electrode portion 53 of the auxiliary electrode member 50 by the auxiliary electrode power supply circuit 240. Therefore, the amount of particulates S can be detected properly. Also, failure of the auxiliary electrode power supply circuit 240 can be prevented.

In the system 1 of the present embodiment, the auxiliary first switch 243 is provided between the auxiliary first output terminal 241 of the auxiliary electrode power supply circuit 240 and the first communicating member 13, and the auxiliary second switch 244 is provided between the auxiliary second output terminal 242 and the extending portion 51 of the auxiliary electrode member 50. When the detection section 10 is driven, these switches are closed. Therefore, the auxiliary electrode portion 53 of the auxiliary electrode member 50 can be driven by the auxiliary electrode power supply circuit 240. Meanwhile, when the degree of insulation between the first discharge electrode 31 of the ion source 11 and the particulate electrifying section 12 (the first potential member), and the extending portion 51 and the auxiliary electrode portion 53 (auxiliary potential member) of the auxiliary electrode member 50 is tested, the switches 243 and 244 are opened. As a result, the auxiliary electrode power supply circuit 240 is disconnected. Therefore, the auxiliary electrode power supply circuit 240 can be protected from the test voltage Vm2 which is applied when the degree of insulation (insulating performance) is tested. In addition, the degree of insulation between the first discharge electrode 31 of the ion source 11 and the particulate electrifying section 12 (the first potential member), and the extending portion 51 and the auxiliary electrode portion 53 (auxiliary potential member) of the auxiliary electrode member 50 can be tested properly without being affected by the auxiliary electrode power supply circuit 240.

Notably, as to the particulate electrifying section 12, the extending portion 51 of the auxiliary electrode member 50, and the heater-equipped auxiliary electrode insulating pipe 79, which are a portion of the members used in the present embodiment, the first discharge potential PV1, which is the potential of the particulate electrifying section 12, corresponds to the first potential in the present invention. The auxiliary electrode potential PV3, which is the potential of the extending portion 51 and the auxiliary electrode portion 53 of the auxiliary electrode member 50, corresponds to the second potential in the present invention. The auxiliary electrode power supply drive circuit 240 corresponds to the drive circuit and the auxiliary electrode drive circuit in the present invention.

The first discharge electrode 31 of the ion gas jetting source 11, the particulate electrifying section 12, and the first communicating member 13 correspond to the first potential member, and the extending portion 51 and the auxiliary electrode portion 53 of the auxiliary electrode member 50 correspond to the second potential member and the auxiliary potential member. The extending portion 51 of the auxiliary electrode member 50 corresponds to the auxiliary electrode communicating member.

The auxiliary electrode insulating pipe 77 and the insulating ceramic layer 76 of the heater-equipped auxiliary electrode insulating pipe 79 correspond to the insulating member.

Moreover, in the system 1 of the present embodiment, when the tested degree of insulation is low, the drive of the detection section 10 by the ion source power supply circuit 210 and the auxiliary electrode power supply circuit 240 is stopped. By virtue of this, when the degree of insulation (insulating performance) is low, in particular, when the degree of insulation (insulating performance) is extremely low (a short circuit is formed), it is possible to reliably prevent occurrence of problems such as failures of the ion source power supply circuit 210 and the auxiliary electrode power supply circuit 240 themselves, and failure of the detection section 10, which failures would otherwise occur due to drive of the ion source power supply circuit 210 and the auxiliary electrode power supply circuit 240.

Moreover, in the system 1 of the present embodiment, the test voltage Vm1, Vm2 is applied between the first potential member (the first communicating member 13, the particulate electrifying section 12) and the second potential member (the outer enclosing portion 14 (the ground potential member), the extending portion 51 (the auxiliary electrode communicating member) of the auxiliary electrode member 50), and the degree of insulation between the first potential member 13, 12 and the second potential member 14, 51 is tested on the basis of the magnitude of the leak current Im1, Im2 flowing therebetween.

Since this method only requires application of the test voltage between the first potential member 13, 12 and the second potential member 14, 51 and detection of the leak current Im1, Im2 flowing therebetween, the degree of insulation (insulating performance) can be readily tested.

Moreover, in the system 1 of the present embodiment, in the case where the degree of insulation between the first communicating member 13 (the first potential member) and the outer enclosing member 14 (the second potential member, the ground potential member) is low or the degree of insulation between the particulate electrifying section 12 (the first potential member) and the extending portion 51 (the second potential member, the auxiliary potential member) of the auxiliary electrode member 50 is low, the heater 78 is energized so as to heat the insulating member (the first insulating spacer 121, and the auxiliary electrode insulating pipe 77 and the insulating ceramic layer 76 of the heater-equipped auxiliary electrode insulating pipe 79) to thereby recover the insulating performance of the insulating member. Namely, through heating, foreign substances such as water droplets and soot adhering to the insulating member 121, 77, 76 are removed, whereby its insulating performance is recovered. By virtue of this, the present system 1 can perform stable measurement for the exhaust gas EG (the gas under measurement) which contains foreign substances such as water and soot.

The exhaust gas EG flowing through the exhaust pipe EP of the internal combustion engine may contain a large amount of soot (particulates S) and water droplets (in particular, at the time of startup). Therefore, as a result of accumulation of soot on, or adhesion of water droplets to, the insulating member 121, 77, 76 which insulates the first potential member 13, 12 and the second potential member 14, 51 from each other, the insulation performance of the insulating member 121, 77, 76; i.e., the degree of insulation between the first potential member 13, 12 and the second potential member 14, 51, is likely to decrease, which raises the possibility that, even when the detection section 10 is driven, the amount of particulates S cannot be detected properly.

In contrast, in the system 1 of the present embodiment, the degree of insulation between the first potential member 13, 12 and the second potential member 14, 51 is tested, and, when the degree of insulation is high, the detection section 10 is driven. Therefore, the amount of particulates S contained in the exhaust gas EG can be detected properly.

In the above, the present invention has been described on the basis of the system 1 of the embodiment. However, the present invention is not limited to the above-described embodiment, and may be modified freely without departing from the scope of the invention.

For example, in the embodiment, the first insulating spacer 121 (the insulating member) intervenes between the first potential member 13 (the outer circumferential surface 63c of the tubular wall portion 63 of the pipe holder 60) and the inner side surface EPi of the exhaust pipe EP. However, depending on the shapes of the exhaust pipe EP and the outer enclosing portion 14 (the ground potential member (the second potential member)), the embodiment may be configured such that the outer enclosing portion 14 extends to a position inside the exhaust pipe EP and the outer enclosing portion 14 is in contact with the exhaust gas EG (the gas under measurement). In this case, preferably, the insulating member 121 is interposed between the first potential member 13 and the ground potential member 14 (the second potential member).

In the above-described embodiment, the test voltage Vm1, Vm2 is applied between the first potential member 13, 12 and the second potential member 14, 51, and the degree of insulation between the first potential member 13, 12 and the second potential member 14, 51 is tested on the basis of the magnitude of the leak current Im1, Im2 flowing therebetween. However, the method of testing the degree of insulation (insulating performance) is not limited thereto.

For example, the insulation resistance between the first potential member 13, 12 and the second potential member 14, 51 may be measured, or the capacitance between the first potential member 13, 12 and the second potential member 14, 51 may be measured by making use of a capacitance meter or the like.

In the above-described embodiment, both of the first insulating spacer 121 (the distal-end-side surface 121c) and the heater-equipped auxiliary electrode insulating pipe 79 (the distal-end-side surface 79c) are heated by the heater 78. However, the embodiment may be modified to heat one of the first insulating spacer 121 and the heater-equipped auxiliary electrode insulating pipe 79.

In the above-described embodiment, the detection section 10 and the circuit section 201 are connected via the cable 160. However, the embodiment may be modified such that the detection section 10 and the circuit section 201 are disposed to be located adjacent to each other without interposition of the cable 160 therebetween.

DESCRIPTION OF SYMBOLS

EP: exhaust pipe
EPi: inner side surface (of the exhaust pipe)
EPO: mounting opening
EG: exhaust gas
S: particulate
SC: electrified particulate
CP: ion
CPF: floating ion
CPH: exhausted ion
Is: signal current
1: particulate detection system
10: detection section
11: ion gas jetting source (ion source)
DS: discharge space
12: particulate electrifying section (first potential member)
13: first communicating member (first potential member)
14: outer enclosing portion (ground potential member)
20: needlelike electrode member
21: extending portion (of the needlelike electrode member)
22: needlelike distal end portion (of the needlelike electrode member) (second discharge electrode (ion source))
30: nozzle member (ion source, particulate electrifying section)
31: nozzle section (first discharge electrode (ion source), particulate electrifying section, first potential member)
31N: nozzle
PV1: first discharge potential (first potential)
PV2: second discharge potential
PV3: auxiliary electrode potential (second potential)
PVE: ground potential (second potential)
40: mixing/exhausting member (particulate electrifying section)
MX: mixing region
42: capturing electrode
48: lid member (particulate electrifying section)
50: auxiliary electrode member
51: extending portion (of the auxiliary electrode member) (auxiliary electrode communicating member, second potential member, auxiliary potential member)
53: auxiliary electrode section (of the auxiliary electrode member) (auxiliary electrode, second potential member, auxiliary potential member)
60: pipe holder (first communicating member)
61: holding portion (first communicating member)
63: tubular wall portion (of the pipe holder)
76: insulating ceramic layer (insulating member)
77: auxiliary electrode insulating pipe (insulating member)
78: heater
79: heater-equipped auxiliary electrode insulating pipe
80: inner tube (first communicating member)
90: metallic shell (outer enclosing portion)
100: plug member (outer enclosing portion)
110: outer tube (outer enclosing portion)
121: first insulating spacer (insulating member)
160: cable
AK: compressed air (gas)
AR: air (gas)
S3: first insulation test (insulation test means)
S5: second insulation test (insulation test means)
S4, S6: drive permission/prohibition determination means
S14: drive stoppage means
S15-S17: insulation recovery energization instruction means
S31: test-time switch opening instruction means
S51: test-time auxiliary switch opening instruction means
S81: drive-time switch closing instruction means
S82: drive-time auxiliary switch closing instruction means
Vm1, Vm2: test voltage
Im1, Im2: leak current
201: circuit section
202: microprocessor
210: ion source power supply circuit (drive circuit, ion source drive circuit)
211: first output terminal
212: second output terminal
215: ground insulation test circuit (insulation test means)
220: measurement control circuit
225: drive control section
226: heater energization circuit
227: heater energization control section
230: signal current detection circuit
240: auxiliary electrode power supply circuit (drive circuit, auxiliary electrode drive circuit)
241: auxiliary first output terminal
242: auxiliary second output terminal
245: auxiliary electrode insulation test circuit (insulation test means)

The invention claimed is:

1. A particulate detection system for detecting an amount of particulates in a gas under measurement flowing through a gas flow pipe, comprising:
a detection section which is mounted to a mounting opening of the gas flow pipe;
a drive circuit which drives the detection section; and
a drive control section which controls the drive circuit, wherein
the detection section includes
a first potential member which is maintained at a first potential when the detection section is driven by the drive circuit, a second potential member which is maintained at a second potential different from the first potential when the detection section is driven by the drive circuit, and an insulating member which is disposed between the first potential member and the second potential member so as to electrically insulate them from each other;

the system further comprises insulation test means for testing the degree of insulation between the first potential member and the second potential member; and the drive control section includes drive permission/prohibition determination means for determining, on the basis of the degree of insulation tested by the insulation test means, whether to permit the drive of the detection section by the drive circuit.

2. A particulate detection system according to claim 1, wherein the drive control section includes drive stoppage means for stopping the drive of the detection section by the drive circuit when the degree of insulation tested by the insulation test means is low.

3. A particulate detection system according to claim 1, wherein the insulation test means is first test means for applying a test voltage between the first potential member and the second potential member and measuring a leak current flowing between the two members or an insulation resistance between the two members.

4. A particulate detection system according to claim 1, wherein the detection section includes an ion source which has a first discharge electrode and a second discharge electrode and which produces ions by gaseous discharge between these electrodes, a particulate electrifying section which electrically communicates with the first discharge electrode of the ion source and which is configured to mix a portion of the gas under measurement flowing through the gas flow pipe with the ions produced by the ion source and to return to the gas flow pipe electrified particulates which are particulates contained in the part of the gas under measurement and to which the ions adhere, the particulate electrifying section forming a capturing electrode which captures floating ions which are a portion of the ions and which did not adhere to the particulates, a first communicating member which electrically communicates with the first discharge electrode and the particulate electrifying section, a second discharge electrode communicating member which electrically communicates with the second discharge electrode, and a ground potential member which is the second potential member and which is in contact with and electrically communicates with the gas flow pipe and is maintained at a ground potential which is the second potential;

the first discharge electrode of the ion source, the particulate electrifying section, and the first communicating member serve as the first potential member which is maintained at the first potential;

the insulating member intervenes between the first potential member and the gas flow pipe or the ground potential member; and the drive circuit has a first output terminal for supplying electricity to the first discharge electrode of the ion source and the particulate electrifying section through the first communicating member when the detection section is driven, whereby the first discharge electrode and the particulate electrifying section are maintained at the first potential, and a second output terminal for supplying electricity to the second discharge electrode of the ion source through the second discharge electrode communicating member when the detection section is driven such that the second discharge electrode is maintained at a second discharge potential at which discharge occurs between the first discharge electrode and the second discharge electrode;

the drive circuit includes an ion source drive circuit which drives the ion source and the particulate electrifying section; and the drive permission/prohibition determination means determines whether to permit the drive of the ion source and the particulate electrifying section by the ion source drive circuit, on the basis of the degree of insulation between the first potential member, and the gas flow pipe and the ground potential member tested by the insulation test means.

5. A particulate detection system according to claim 4, further comprising:

a first switch which is disposed between the first output terminal and the first communicating member and which establishes and breaks electrical continuity between the first output terminal and the first communicating member;

a second switch which is disposed between the second output terminal and the second discharge electrode communicating member and which establishes and breaks electrical continuity between the second output terminal and the second discharge electrode communicating member;

drive-time switch closing instruction means for closing the first switch and the second switch when the detection section is driven; and test-time switch opening instruction means for opening the first switch and the second switch when the degree of insulation between the first potential member, and the gas flow pipe and the ground potential member is tested by the insulation test means.

6. A particulate detection system according to claim 1, wherein the detection section includes an ion source which has a first discharge electrode and a second discharge electrode and which produces ions by gaseous discharge between these electrodes, a particulate electrifying section which electrically communicates with the first discharge electrode of the ion source and which is configured to mix a portion of the gas under measurement flowing through the gas flow pipe with the ions produced by the ion source and to return to the gas flow pipe electrified particulates which are particulates contained in the part of the gas under measurement and carrying the ions adhering to the particulates, the particulate electrifying section forming a capturing electrode which captures floating ions which are a portion of the ions and which did not adhere to the particulates, a first communicating member which electrically communicates with the first discharge electrode and the particulate electrifying section, an auxiliary electrode which is electrically insulated from the first discharge electrode and the second discharge electrode and which is disposed within the particulate electrifying section so as to assist the capturing of the floating ions by the capturing electrode, and an auxiliary electrode communicating member which electrically communicates with the auxiliary electrode;

the first discharge electrode of the ion source, the particulate electrifying section, and the first communicating member serve as the first potential member which is maintained at the first potential;

the auxiliary electrode and the auxiliary electrode communicating member serve as an auxiliary potential member which is the second potential member and is maintained at an auxiliary electrode potential which is the second potential;

the insulating member is disposed between the particulate electrifying section and the auxiliary electrode communicating member;

the drive circuit has an auxiliary first output terminal which electrically communicates with the first discharge electrode of the ion source and the particulate electrifying section through the first communicating member when the detection section is driven, whereby the auxiliary first output terminal is maintained at the first potential, and an auxiliary second output terminal for supplying electricity to the auxiliary electrode via the auxiliary electrode communicating member when the detection section is driven such that the auxiliary electrode is maintained at the auxiliary electrode potential;

the drive circuit includes an auxiliary electrode drive circuit which drives the auxiliary electrode; and the drive permission/prohibition determination means determines whether to permit the drive of the auxiliary electrode by the auxiliary electrode drive circuit, on the basis of the degree of insulation between the first potential member, and the auxiliary potential member tested by the insulation test means.

7. A particulate detection system according to claim 6, further comprising:

an auxiliary first switch which is disposed between the auxiliary first output terminal and the first communicating member and which establishes and breaks electrical continuity between the auxiliary first output terminal and the first communicating member;

an auxiliary second switch which is disposed between the auxiliary second output terminal and the auxiliary electrode communicating member and which establishes and breaks electrical continuity between the auxiliary second output terminal and the auxiliary electrode communicating member;

drive-time auxiliary switch closing instruction means for closing the auxiliary first switch and the auxiliary second switch when the detection section is driven; and test-time auxiliary switch opening instruction means for opening the auxiliary first switch and the auxiliary second switch when the degree of insulation between the first potential member, and the auxiliary potential member is tested by the insulation test means.

8. A particulate detection system according to claim 1, further comprising:

a heater for heating the insulating member;

a heater energization circuit for supplying electricity to the heater; and a heater energization control section for controlling the heater energization circuit, wherein the heater energization control section includes insulation recovery energization instruction means, operable when the degree of insulation tested by the insulation test means is low, for instructing the heater energization circuit to supply electricity to the heater so as to heat the insulating member, to thereby recover the degree of insulation.

9. A particulate detection system according to claim 1, wherein the gas flow pipe is an exhaust pipe of an internal combustion engine; and the gas under measurement is exhaust gas flowing through the exhaust pipe.

* * * * *